United States Patent
Simmons et al.

(10) Patent No.: US 10,052,418 B2
(45) Date of Patent: Aug. 21, 2018

(54) BREASTMILK EXPRESSION SYSTEM WITH DETECTION, FEEDBACK AND CONNECTABILITY FEATURES

(71) Applicant: MEDELA HOLDING AG, Baar (CH)

(72) Inventors: Bryan D. Simmons, North Aurora, IL (US); John R. Skach, Cary, IL (US); Ryan Bauer, Fox River Grove, IL (US); Deanna Gilbert, Arlington Heights, IL (US); David Cho, Arlington Heights, IL (US)

(73) Assignee: MEDELA HOLDING AG, Baar (CH)

( * ) Notice: Subject to any disclaimer, the term of this patent is extended or adjusted under 35 U.S.C. 154(b) by 0 days.

(21) Appl. No.: 15/091,286

(22) Filed: Apr. 5, 2016

(65) Prior Publication Data

US 2016/0287767 A1 Oct. 6, 2016

Related U.S. Application Data

(60) Provisional application No. 62/143,634, filed on Apr. 6, 2015.

(51) Int. Cl.
*A61M 1/06* (2006.01)
*A61M 1/00* (2006.01)

(52) U.S. Cl.
CPC .............. *A61M 1/062* (2014.02); *A61M 1/06* (2013.01); *A61M 1/0031* (2013.01);
(Continued)

(58) Field of Classification Search
CPC .......... A61M 2005/14208; A61M 1/06; A61M 2205/3331; A61M 2205/15
See application file for complete search history.

(56) References Cited

U.S. PATENT DOCUMENTS 3,962,905 A * 6/1976 Jouve .................. F17D 5/06
 73/40.5 R
5,380,280 A 1/1995 Peterson
(Continued)

FOREIGN PATENT DOCUMENTS

EP 2538193 A1 12/2012
WO WO-2013/166462 A1 11/2013

OTHER PUBLICATIONS

International Search Report and Written Opinion, International Application No. PCT/IB2016/000592, dated Aug. 5, 2016.

*Primary Examiner* — Bhisma Mehta
*Assistant Examiner* — Matthew A Engel
(74) *Attorney, Agent, or Firm* — Marshall, Gerstein & Borun LLP

(57) ABSTRACT

Methods and systems for an improved feedback milk extraction system are described. According to aspects, the system may communicate with various electronic devices and/or server components to exchange data and perform certain functionalities. The functionalities may include providing visual and audio feedback to a user, supporting unique kit identification as well as associated user profiles and preferred configuration settings, detecting and responding to leaks having various sizes during operation of the breastpump, controlling operation of the breastpump in response to detected leaks and the detected type and/or magnitude of the leak, preemptively contacting customers if a fault condition is detected or imminent, enabling effective labeling of collection containers, and determining volume and flow of expressed breastmilk.

7 Claims, 8 Drawing Sheets

(52) U.S. Cl.
CPC ....... *A61M 1/0068* (2014.02); *A61M 2205/15* (2013.01); *A61M 2205/18* (2013.01); *A61M 2205/332* (2013.01); *A61M 2205/3331* (2013.01); *A61M 2205/3334* (2013.01); *A61M 2205/3379* (2013.01); *A61M 2205/3553* (2013.01); *A61M 2205/3561* (2013.01); *A61M 2205/3576* (2013.01); *A61M 2205/502* (2013.01); *A61M 2205/702* (2013.01)

(56) References Cited

U.S. PATENT DOCUMENTS

| | | | |
|---|---|---|---|
| 5,540,083 A * | 7/1996 | Sato | G01M 3/2876 73/40 |
| 5,630,710 A * | 5/1997 | Tune | A61M 5/172 417/326 |
| 5,658,133 A * | 8/1997 | Anderson | A61M 5/172 417/479 |
| 5,670,050 A * | 9/1997 | Brose | A61L 2/04 210/646 |
| 5,676,525 A | 10/1997 | Berner et al. | |
| 6,109,100 A | 8/2000 | Buckley et al. | |
| 6,299,594 B1 | 10/2001 | Silver | |
| 6,481,986 B1 | 11/2002 | Silver et al. | |
| 6,547,756 B1 | 4/2003 | Greter et al. | |
| 6,676,631 B1 | 1/2004 | Greter | |
| 7,347,836 B2 | 3/2008 | Peterson et al. | |
| 7,517,332 B2 * | 4/2009 | Tonelli | A61M 1/3672 222/22 |
| 7,766,873 B2 * | 8/2010 | Moberg | A61M 5/145 604/131 |
| 8,057,425 B1 | 11/2011 | Myers et al. | |
| 8,070,715 B2 | 12/2011 | Quackenbush et al. | |
| 8,070,716 B2 | 12/2011 | Sutrina et al. | |
| 8,142,393 B2 | 3/2012 | Myers | |
| 8,216,179 B2 | 7/2012 | Bosshard et al. | |
| 8,267,893 B2 * | 9/2012 | Moberg | A61M 5/5086 604/151 |
| 8,313,308 B2 * | 11/2012 | Lawless | A61M 5/14224 417/44.1 |
| 8,376,986 B2 | 2/2013 | Van Schijndel et al. | |
| 8,617,101 B2 | 12/2013 | Tack | |
| 8,647,074 B2 * | 2/2014 | Moberg | A61M 5/145 417/19 |
| 8,663,200 B2 * | 3/2014 | Weston | A61M 1/0031 604/540 |
| 8,681,010 B2 * | 3/2014 | Moberg | A61M 5/145 340/606 |
| 8,734,386 B2 | 5/2014 | Jager-Waldau | |
| 8,827,947 B2 | 9/2014 | Bosman et al. | |
| 8,926,556 B2 | 1/2015 | Van Eijkelenborg et al. | |
| 9,199,018 B2 * | 12/2015 | Bauer | A61M 1/06 |
| 9,320,851 B2 * | 4/2016 | Regittnig | A61M 5/16836 |
| 9,370,612 B2 * | 6/2016 | Bauer | A61M 1/06 |
| 9,375,523 B2 | 6/2016 | Sella et al. | |
| 2005/0043677 A1 | 2/2005 | Kelly et al. | |
| 2005/0234370 A1 | 10/2005 | Beal et al. | |
| 2007/0191770 A1 * | 8/2007 | Moberg | A61M 5/145 604/131 |
| 2007/0213662 A1 * | 9/2007 | Kalafut | A61M 5/14546 604/96.01 |
| 2008/0009815 A1 | 1/2008 | Grabenkort et al. | |
| 2008/0177224 A1 | 7/2008 | Kelly et al. | |
| 2009/0090186 A1 * | 4/2009 | Linzenkirchner | G01H 1/00 73/587 |
| 2010/0100075 A1 * | 4/2010 | Weston | A61M 1/0031 604/543 |
| 2010/0125246 A1 * | 5/2010 | Kalpin | A61M 5/14276 604/151 |
| 2010/0145303 A1 * | 6/2010 | Yodfat | A61M 5/1408 604/506 |
| 2010/0217192 A1 * | 8/2010 | Moberg | A61M 5/145 604/151 |
| 2011/0071466 A1 | 3/2011 | Silver et al. | |
| 2012/0116298 A1 | 5/2012 | Van Schijndel et al. | |
| 2012/0259282 A1 * | 10/2012 | Alderete, Jr. | A61M 5/14244 604/131 |
| 2013/0073211 A1 | 3/2013 | Hershkovich | |
| 2014/0263611 A1 * | 9/2014 | Bauer | A61M 1/06 235/375 |
| 2014/0378895 A1 | 12/2014 | Barack | |
| 2015/0133829 A1 * | 5/2015 | DeBusk | A61F 13/00068 601/6 |
| 2016/0022886 A1 * | 1/2016 | Bauer | A61M 1/06 604/67 |
| 2016/0184496 A1 * | 6/2016 | Jaecklein | A61M 1/0001 604/318 |
| 2016/0296680 A1 * | 10/2016 | Simmons | A61M 1/06 |
| 2017/0087285 A1 * | 3/2017 | Bauer | A61M 1/06 |

* cited by examiner

… (US 10,052,418 B2)

BREASTMILK EXPRESSION SYSTEM WITH DETECTION, FEEDBACK AND CONNECTABILITY FEATURES

CROSS-REFERENCE TO RELATED APPLICATIONS

This application claims benefit of the filing date of U.S. Provisional Patent Application No. 62/143,634 (filed Apr. 6, 2015 and entitled "IMPROVED BREASTMILK EXPRESSION SYSTEM WITH DETECTION, FEEDBACK AND CONNECTABILITY FEATURES"), the disclosure of which is hereby incorporated by reference in its entirety.

FIELD OF THE DISCLOSURE

The present disclosure generally relates to an improved breastmilk expression system. More particularly, the present disclosure relates to an improved breastmilk expression system, configured to effectively detect and distinguish various deviations within the system, such as leaks or milk flow, and support communication between the system and a set of additional devices to facilitate various applications and functionalities.

BACKGROUND

A breastmilk expression system, or extracting system, such as a breastpump system, compression system, or any other suitable system is a mechanical device capable of extracting milk from the breasts of a lactating woman. There are many types of manual or electronic milk extracting systems such as piston pumps, rotary vane pumps, diaphragm pumps, and others. Generally, a user of a milk extracting system will use the milk extracting system during a pumping session that lasts a certain amount of time. The pumping session results in a collection of milk that is expressed from the breasts during the session, where the milk may be collected in bottles, bags, or other containers.

There is an opportunity for improved feedback milk extracting systems that facilitate various feedback and interaction with users. Further, there is an opportunity to support various communications among peripheral electronic devices and milk extracting systems, and various applications relating thereto.

SUMMARY

According to an embodiment, a breastmilk extracting system may be provided. The breastmilk extracting system may include a pressure measurement component configured to obtain a pressure level in the system during operation of the system; a comparison circuit configured to, on a substantially continuous basis, compare at least one of a displacement measurement and motor current data to the pressure level to obtain a comparison result, determine that there is a leak in the system when the comparison result at least meets a threshold value, and estimate a magnitude of the leak; and at least one feedback component configured to indicate to a user the existence of the leak in the system.

According to another embodiment, a method for operating a breastmilk extracting system may be provided. The method may include obtaining, by a pressure measurement component, a pressure level in the system during operation of the system; on a continuous basis, comparing at least one of a displacement measurement and motor current data to the pressure level to obtain a comparison result; when the comparison result at least meets a threshold value, determining that there is a leak in the system, and estimating a magnitude of the leak; and indicating, to a user by at least one feedback component, the existence of the leak in the system.

According to another embodiment, a method of detecting leaks within a breastmilk extracting system may be provided. The method may include determining, by a processor at a first point in time, (i) a first absolute pressure within the system and (ii) an initial displaced volume; determining, by the processor at a second point in time, (i) a second absolute pressure within the extracting system and (ii) a second displaced volume; determining an original volume of the system; estimating a leaked volume of the system; comparing a difference between the original volume and the leaked volume to a threshold value to determine if there is a leak in the system and to produce a resulting comparison where the leak is present; based on the comparing, determining an action to take to address the leak, where the action differs for leaks of different sizes; and performing the action.

In another embodiment, a breastmilk extracting system may be provided. The system may include a leak detection system connectable to a controller, the leak detection system configured to determine a leak arising during a cycle in the system during delivery of the cycle of a pumping pattern using a leak volume calculation.

In another embodiment, a breastmilk extracting system may be provided. The system may include a leak detection circuit configured to determine a leak; and a response circuit connectable to the leak detection circuit, the response circuit selectively providing feedback from the leak detection circuit during a pumping session while selectively enabling continued use of the system and corrective operation based on a magnitude of the leak detected by the leak detection circuit.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION OF THE PREFERRED EMBODIMENTS

Figure 1:
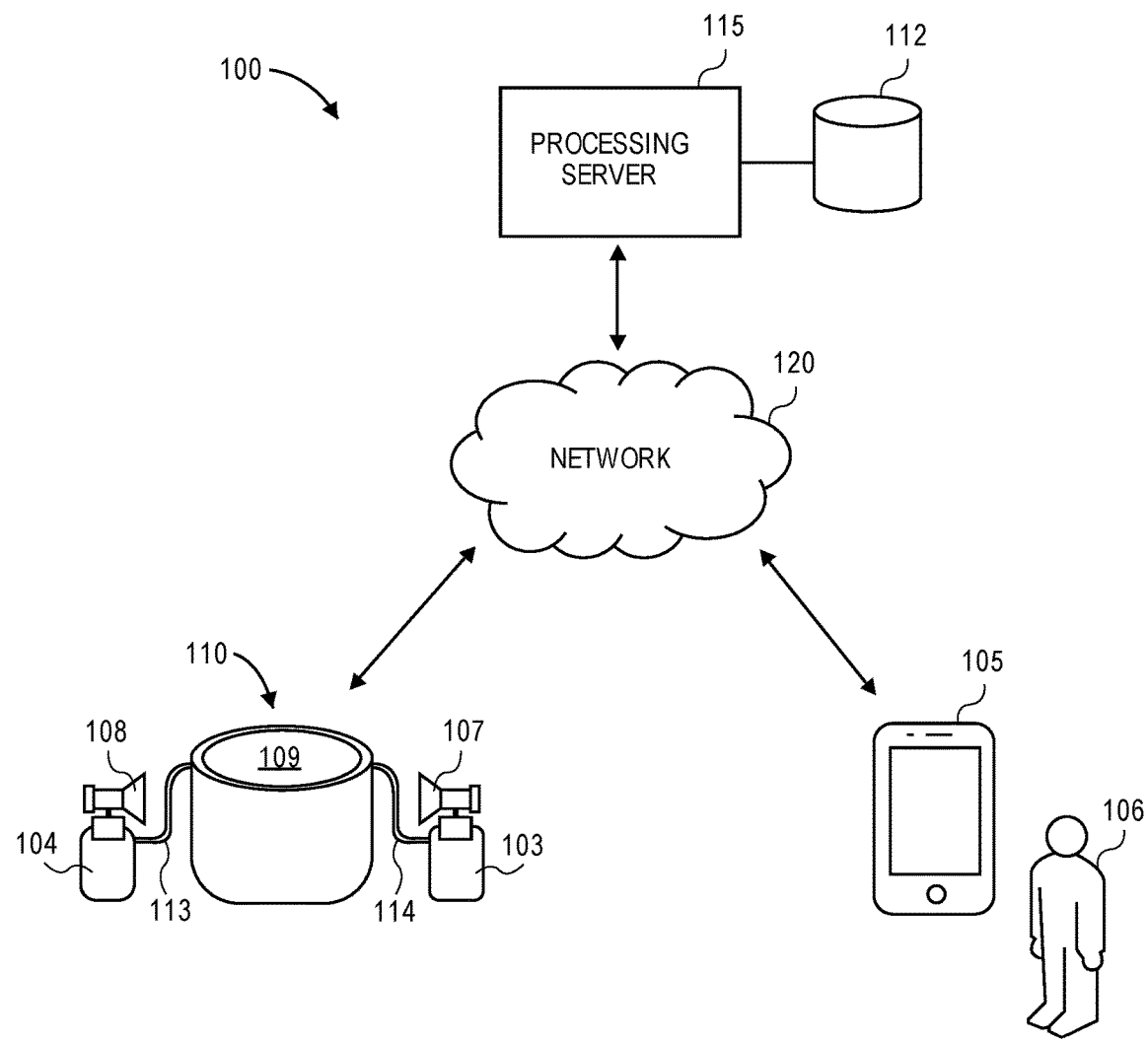
FIG. 1 depicts a system including various components and entities associated with an improved feedback milk extracting system and electronic devices associated therewith, in accordance with some exemplary embodiments.

FIG. 1 depicts an exemplary system 100 that can include one or more actions and/or feedback in response to a deviation in the system, such as a leak or milk flow, detected during operation. The system can distinguish between leaks of various sizes based on a signal analysis, and can enable a system action and/or feedback based on the size of the leak detected. The system 100 can further support various functionalities associated with an improved milk extracting system, or breastmilk expression system, such as a breastpump system, compression system, or any other suitable system for expressing milk, and various devices and components that can be associated therewith that improve ease of operation and/or feedback experienced during operation of the system. Although FIG. 1 depicts certain connectable entities, components, and devices, it should be appreciated that any additional or alternate entities and components can be incorporated into the system, as desired, to achieve a variety of functional advantages, examples of which are set forth in accordance with the principles herein.

As illustrated in FIG. 1, the system 100 includes a suitable breastmilk expression system, such as a breastpump system 110, an electronic device 105 that can be selectively connected to the breastpump system 110, and a processing server 115 that can be selectively connected to either or both of the breastpump system 110 and the electronic device 105.

Generally, the electronic device 105 may be any type of electronic device capable of computation and engaging at least one or a plurality of network communications such as, for example, a television, smartphone, notebook computer, tablet, phablet, GPS (Global Positioning System) or GPS-enabled device, printer, smart watch, smart glasses, smart bracelet, wearable electronic device, PDA (personal digital assistant), pager, computing device configured for wireless communication, and/or the like. The electronic device 105 may be operated by a user 106 or, in some implementations, may be operated autonomously by processing logic and/or various sensors.

The electronic device 105 may include a user interface configured to display certain information and receive selections and inputs from the user 106. Further, the electronic device 105 is capable of supporting a communication platform, such as a dedicated application or other type of software (generally, an "application").

In operation, the user 106 may interface with the application via the user interface to make selections, input data, initiate or facilitate communications with other components of the system 100, and/or perform other functions. According to the present exemplary embodiments, the application may be a breastpumping application that includes functionalities associated with recording data locally with the device 105 before, during, and/or after a breastpumping session with the breastpump system 110.

Generally, the breastpump system 110 may be a mechanical device including various components configured to extract milk from the breasts of a lactating woman. To achieve this, the breastpump system 110 may use suction to act on the nipples of the breasts within a set of breastshields 107, 108, or milk can be extracted by compressive force, or by other suitable alternatives. The suction achieved using various extraction methods may mimic an infant's sucking action, whereby the suction causes milk within the breast to evacuate into a set of bottles 103, 104, or other suitable collection container for collection. The breastpump system 110 may be of any type, such as a piston pump which may draw a volume displacement mechanism, such as a piston, through a cylinder to create suction, a rotary vane pump which may use a cam with retractable vanes to create suction, a diaphragm pump which may use a volume displacement mechanism in the form of a diaphragm acted on by a lever to create suction with each stroke, or another type of pump, compression device, or other milk extraction device. The depiction of the breastpump system 110 in FIG. 1 is merely exemplary and it should be appreciated that different types and sizes of breastpumps having different components are envisioned.

The breastpump system 110 may include a user interface 109 configured to display certain information and receive selections and inputs from a user. In particular, the user may enter various operation parameters for the breastpump system 110 via the user interface 109. For example, the user may initiate or end a breastpumping session, activate or mute feedback sounds, enter a goal time and/or a suction level for a breastpumping session, and/or the like. The user interface 109 may also display certain parameters associated with its operation including, for example, an elapsed time or time remaining for a breastpumping session, a suction level, a current time, a status for a breastpumping session (e.g., active, paused, error), warning or error conditions (e.g., leak detected), and/or other information.

Generally, the user interface 109 may support a combination of visual and audio feedback throughout a breastpumping session to help guide the user during a pumping session. For example, the visual, tactile and/or audio feedback may be used to indicate an error, a "go no further" condition, or that the breastpump system 110 is ready to operate.

Figure 3:
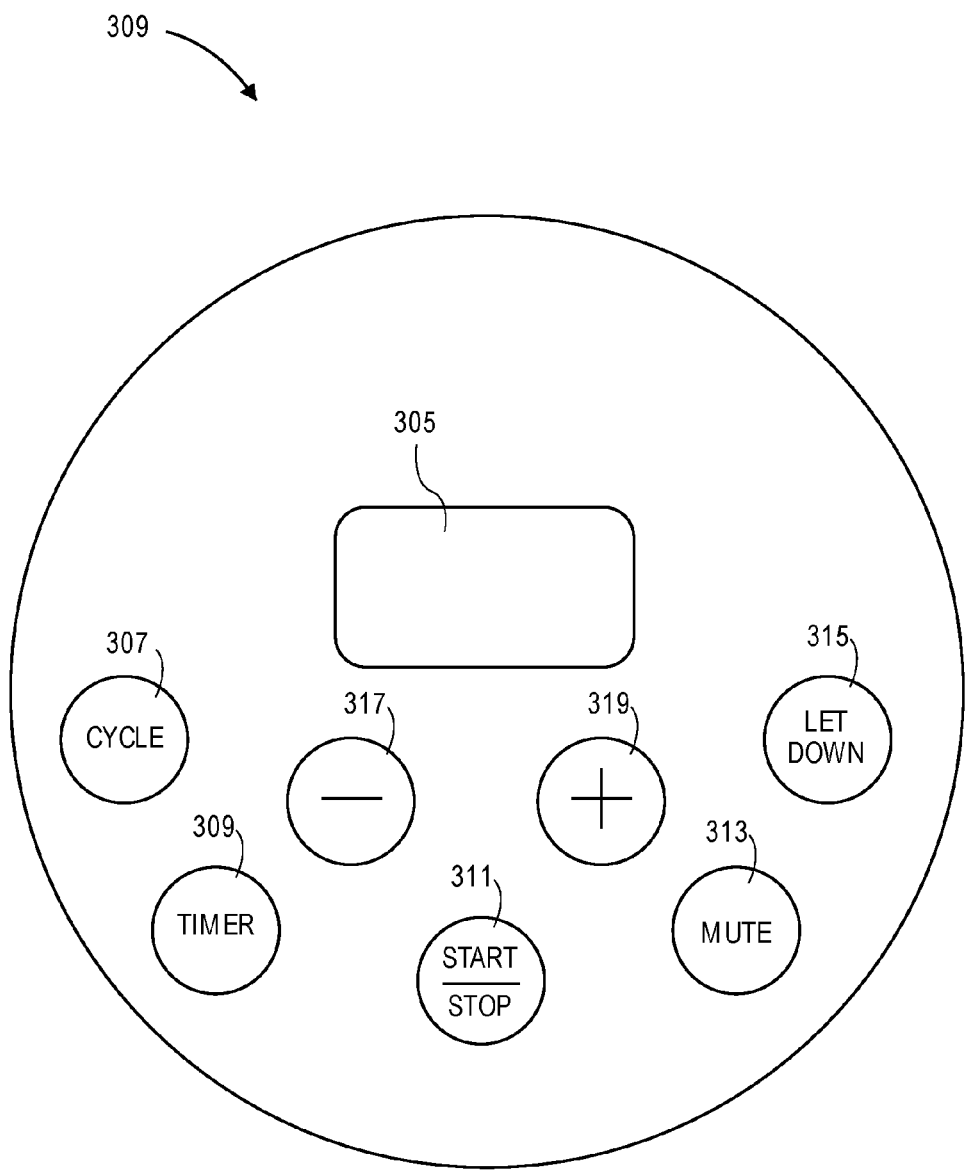
FIG. 3 illustrates an exemplary user interface constructed in accordance with the principles herein.

FIG. 3 depicts a more detailed view of a user interface 309 of a breastpump system, such as the user interface 109 as described with respect to FIG. 1. It should be appreciated that the user interface 309 is merely exemplary, and may include additional or alternative content, selections, shapes, sizes, and/or the like. The user interface 109 may include a set of selections that enables a user to operate the breastpump system and facilitate certain functionalities of the breastpump system. Each of the set of selections is selectable by the user of the breastpump system to cause the breastpump system to perform a corresponding action or function.

As depicted in FIG. 3, the user interface 309 may include a start/stop selection 311 and a timer selection 309. Selection of the start/stop selection 311 by the user causes the breastpump system to start operation if the breastpump system is currently stopped or paused, or stop/pause operation if the breastpump system is currently operating. Selection of the timer selection 309 by the user may enable the user to enter a timeout period for operation of the breast pump system. In some implementations, the user interface 109 may include at least one feedback component, such as a display 305 (e.g., an LED display or an LCD display) that displays the timeout period that the user may set via the timer selection 309. The set of selections may further include a "+" selection 319 and a "−" selection 317 which the user may select in coordination with setting and/or modifying the timer to respectively add time to the timeout period or remove time from the timeout period.

The set of selections may further include a cycle selection 307 that, when selected by the user, causes the breastpump system to toggle between or among various breastpump system operating cycles. Additionally, the set of selections may include a mute selection 313 and a let down selection 315. Selection of the mute selection 313 by the user may cause the breastpump system to mute (or unmute, if the breastpump system is currently muted) any audio output, including chimes, beeps, tones, and/or the like. Selection of the let down selection 315 may cause the breastpump system to enter (or exit) a "let down" mode that may simulate an infant's sucking pattern/rate to stimulate let-down reflex.

In operation, the breastpump can provide numerous user inputs and various types of feedback, including directive feedback, if desired, to the user via a suitable user interface, such as the interface illustrated in FIG. 3. For example, a user can select a button on the user interface 109, or talk to the pump using voice recognition technology, which may cause the breastpump system 110 to generate a sound, tone, vibration or some other form of haptic feedback, unless the breastpump operating state prohibits the feedback, for example when the device is mute. Voice recognition can be achieved as discussed in U.S. Pat. No. 8,216,178, of common ownership, incorporated herein in its entirety by reference. Further, the breastpump system 110 may generate sounds for any or all of the following conditions, or other conditions as desired: selection of the "+/−" buttons, a timer at zero, a timer at max time; when a "call" alert is determined and/or displayed to indicate the need to call customer service, when a leak is detected; selection of the power up button, selection of a pattern or when the user has exceeded a maximum or minimum vacuum limit available, when the timer has a certain amount of time remaining, and when the timer has expired.

The breastpump system 110 further supports various visual feedback that may be in combination with the audio feedback. In particular, the breastpump system 110 may display a charging indicator when the breastpump system 110 is connected to external power. Further, the breastpump system 110 may support backlighting for one, some, or all audio cues. For example, when the breastpump system 110 generates an alert sound, the breastpump system 110 may display an amber color; and if the breastpump system 110 then switches back to a normal state after an alert, the breastpump system 110 may cease the alert sound and the display of the amber color.

Generally various features are capable of being enabled or disabled based on breastpump operating state. Visual, audio, or haptic cues can be used to indicate the enabled or disabled state of the input feature. As an additional example, once a user reaches a maximum suction level for the breastpump system 110 and the user continues to select "+" on the user interface 109, then the breastpump system 110 may discontinue illuminating the plus sign and may generate an audio cue indicating that a higher suction level is not available. Similarly, once a user reaches a minimum suction level for the breastpump system 110 and the user continues to select "−" on the user interface 109, then the breastpump system 110 may discontinue illuminating the minus sign and may generate an audio cue indicating that a lower suction level is not available.

In certain implementations, the suction levels indicated by the breastpump system 110 may represent a percentage of a selected nominal curve. The suction levels may be tied to other linear or non-linear curves, such as a bell curve, where the change amount for the levels may be linear or non-linear.

In some scenarios, the user of the breastpump system 110 may be the user 106. In other scenarios, the user of the breastpump system 110 may be a user other than the user 106. Although the system of FIG. 1 depicts a single electronic device 105 and a single breastpump system 110, it should be appreciated that the system 100 may include multiple amounts and types of electronic devices and/or breastpump systems.

The system 100 may further include a processing server 115 that may include any combination of hardware and software components associated with any individual, group of individuals, company, corporation, or other type of entity. For example, the processing server 115 may be associated with any or all of a manufacturer, retailer, or servicer of the breastpump system 110. For further example, the processing server 115 may be associated with a health care institution such as a hospital or clinic. The processing server 115 may include or be connected to a database 112 or storage that is configured to store certain information and data. The database 112 may include one or more forms of volatile and/or non-volatile, fixed and/or removable memory. Further, the database 112 may be contained in a single location (e.g., on the same premises as the processing server 115) or distributed across multiple locations.

As illustrated in FIG. 1, the system 100 may further include one or more networks 120 configured to facilitate communications between and among the breastpump system 110, the electronic device 105, and the processing server 115. The network(s) 120 can facilitate any type of data communication via any standard or technology. In some implementations, the network(s) 115 may support various short range communications between the electronic device 105 and the breastpump system 110. The network(s) 120 may also support any wired connection between and among the components of the system 110.

Generally, each of the electronic device 105 and the exemplary breastmilk expression system, or breastpump system 110 may generate or collect data or information and communicate the data or information to the other entities of the system 100 via the network(s) 120. For example, the electronic device 105 and/or the breastpump system 110 may communicate any generated or collected data to the processing server 115 via the network(s) for storage on the database 112. In some implementations, the electronic device 105 and the breastpump system 110 may exchange operation commands via a short range communication, thus enabling remote operation of the breastpump system 110 by the electronic device 105. In some situations, a user (e.g., the user 106) may manually input data or make various selections into the electronic device 105 and/or the breastpump system 110 (e.g., via the respective user interfaces). Each of the electronic device 105 and the breastpump system 110 may be configured with a memory to locally store various data and information.

As discussed herein, the electronic device 105 is capable of supporting a breastpumping application that includes functionalities associated with recording data before, during, and/or after a breastpumping session with the breastpump system 110. The user 106 or breastpump system 110 may communicate interactively with the application to make selections, input data, initiate or facilitate communications with other components of the system 100, and/or perform other functions via the electronic device 105 or the breastpump system. For example, the user 106 or breastpump system 110 may input the volume of milk collected during a breastpumping session; the time, date, and location of the breastpumping session; the duration of the breastpumping session; a frequency of use of the breastpump system 110; performance data related to the breastpump system 110; the suction level(s) used during the breastpumping session; and/or other data.

As discussed herein, the breastpump system 110 may offer various device settings and may enable the user 106 to select certain levels for the settings. For example, the user 106 may prefer a certain goal time, a certain suction level, and/or other settings. The preferred settings for operation of the breastpump system 110 by the user 106 may be compiled into a set of configuration settings for the user 106. According to embodiments, the electronic device 105, and/or the breastpump system 110 may be configured with persistent storage capable of storing the set of configuration settings for the user 106.

In one implementation, the breastpump system 110 may transmit, to the electronic device 105, settings of the breastpump system 110 corresponding to a current or completed breastpumping session by the user 106, where the electronic device 105 may store the settings as a set of configuration settings for the user 106. Accordingly, for subsequent uses of the breastpump system 110 or any other breastpump by the user 106, the electronic device 105 may transmit the set of configuration settings for the user 106 to the corresponding breastpump prior to the user 106 starting a breastpumping session. Upon receipt of the set of configuration settings, the corresponding breastpump may automatically configure its settings. In this regard, the user 106 may not need to manually adjust the breastpump system 110 before each pumping session. This may be useful in situations in which there may be multiple available breastpumps, if the user 106 purchases a new breastpump, or if the user otherwise wishes to use a breastpump that she has yet to use under her most recent configuration selections.

The communications between the electronic device 105 and the breastpump system 110 may be facilitated according to various techniques and channels. In one implementation, the electronic device 105 and/or the breastpump system 110 may support an application programming interface (API) via which the electronic device 105 and/or the breastpump system 110 may request, retrieve, and send data including user feedback and alerts, such as a leak detection alert back and forth between the electronic device 105 and the breastpump system 110. The communications may also be "push" where either the electronic device 105 or the breastpump system 110 sends data to the other component, or "pull" where either the electronic device 105 or the breastpump system 110 requests data from the other component. For example, upon connecting to the breastpump system 110, the electronic device 105 may automatically send the set of configuration settings to the breastpump system 110. Alternatively, upon connecting to the electronic device 105, the breastpump system 110 may request the set of configuration settings from the electronic device 105.

Figure 2:
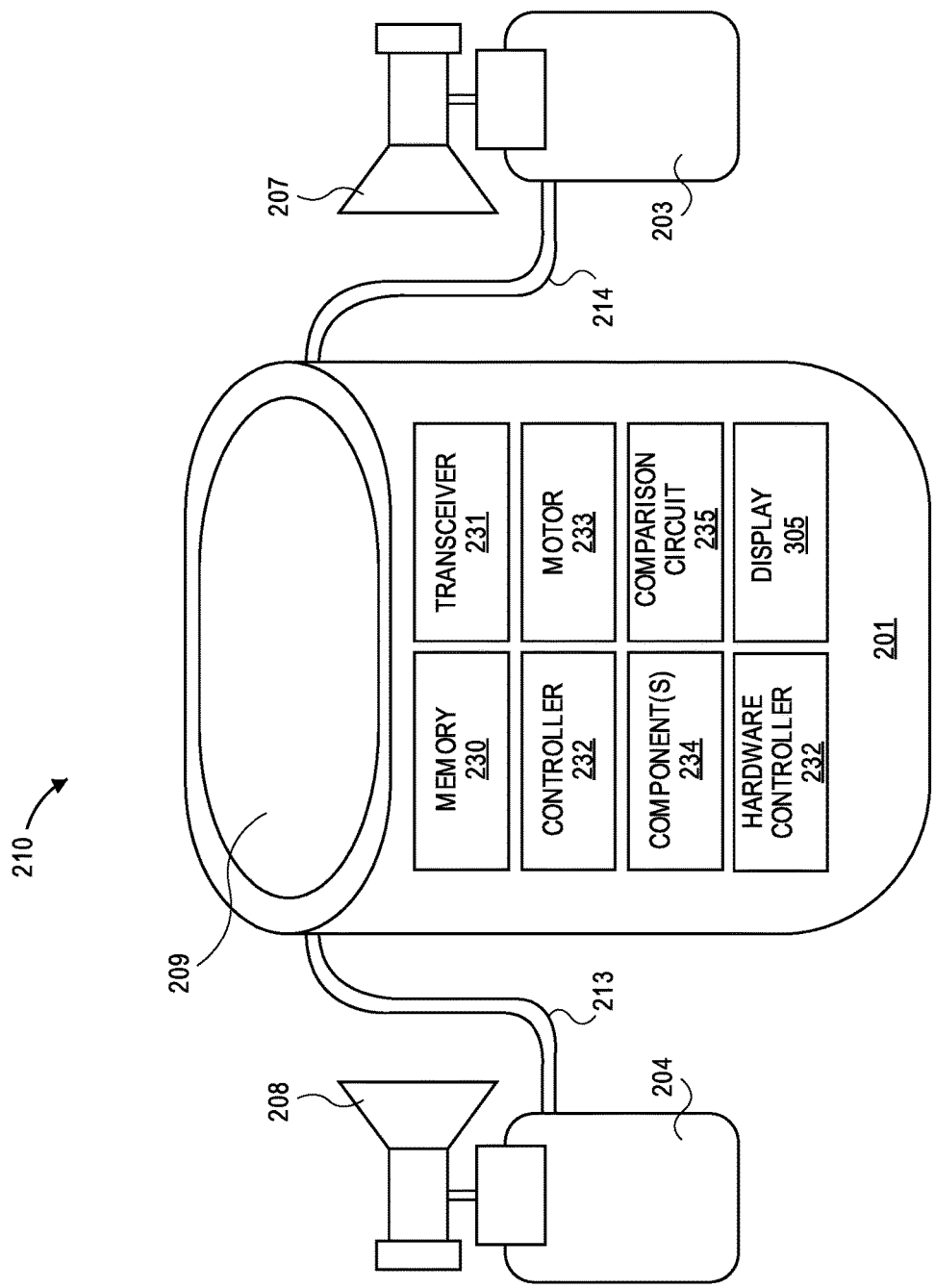
FIG. 2 depicts a more detailed depiction of an improved feedback milk extracting system, in accordance with some exemplary embodiments.

Referring to FIG. 2, depicted is a more detailed schematic of an exemplary breastmilk expression device, or breastpump system 210. The breastpump system 210 may include a breastpump housing 201 portion as well as a "kit" or portable components. Generally, the breastpump housing 201 can house internal components such as a powering component (e.g., a motor 233), and a mechanism for generating pressure to extract milk (e.g., a piston within a cylinder or other suitable mechanism). The housing can also incorporate various external components, such as a user interface 209, a plug or other interface to a power source, and a set of batteries or battery pack that can be connected externally, or internally if desired. Further, the kit may include a set of breastshields 207, 208, a set of bottles 203, 204, tubing components 213, 214, as well as other components not depicted in FIG. 2 including membranes, diaphragms, valves, and/or the like. It should be appreciated that additional or alternative components for the breastpump housing 201 and the kit of the breastpump system 210 are envisioned.

In operation, a user of the breastpump system 210 may disconnect the components of the kit from the breastpump housing 201 for purposes of cleaning or transporting the kit. The kit further enables the user to use a different breastmilk expression system or breastpump other than the breastpump system 210 to complete a breastpumping session. For example, the user may have one breastpump system at home and another breastpump system in the office.

According to embodiments of the present disclosure, the kit may have a unique identification that may serve to distinguish the kit from other kits belonging to other users, and help to avoid unnecessary leak alerts that can occur during operation. Particularly, the kit may locally store or secure an alphanumeric or graphic identification that is detectable by electronic components associated with the breastpump system 210, or incorporated into the breastpump housing 201. For example, the kit may be equipped with an NFC tag that stores the identification and that is readable by an NFC tag reader incorporated into the breastpump housing 201. Alternatively, the kit may be equipped with any suitable device that stores identification information, such as a bar code or any other device. For further example, the breastpump housing 201 may include an imaging sensor capable of capturing an image of the kit identification. It should be appreciated that additional or alternate components may store or otherwise include or display the kit identification.

In some embodiments, a user may manually enter the identification of the kit using the breastpump interface 209 or into an associated electronic device. In other embodiments the kit ID can be provided within a removable memory device and uploaded to associated electronic devices or servers by connecting the memory device to a base as described in European Patent 14 158 098.5 of common ownership, incorporated herein in its entirety. Generally, the kit identification can enable a variety of improved applications and functionalities associated with the breastpump system 210 and entities associated therewith. For example, the kit ID can provide default configuration settings to optimize pump performance to match the kit.

According to some embodiments, the breastpump system 210 may initiate certain functionalities or communications in response to detecting and identifying a kit that is connected thereto. In particular, the breastpump system 210 may connect to an electronic device (e.g., the electronic device 105) to retrieve user profile data that corresponds to the kit identification. In some implementations, the breastpump system 210 may retrieve the user profile data from a dedicated breastpumping application installed on the electronic device. In other implementations, the breastpump system 210 may locally or centrally store the user profile data that corresponds to the kit identification.

In one implementation, the user profile data may include a set of configuration settings that are preferred by the associated user. In operation, the breastpump system 210 may identify the set of configuration settings from the user profile and may automatically implement the set of configuration settings. In this regard, the kit identification enables the user to efficiently and effectively configure different breastpumps according to preferred settings.

Generally, different users may have different techniques of operating the breastpump system 110. Additionally, different users may have different body shapes and, specifically, different breast sizes and breast shapes. As a result, the configuration, operation, and performance of the breastpump system 110 may differ based on its user. For instance, different users may use breastshields of different sizes. According to embodiments, the different user profiles may further include data related to the operation and performance of the breastpump system 110 and/or the kit ID by the corresponding user. The user profile data can therefore enables the breastpump system 110 and/or the electronic device 105 to accurately assess/analyze operation of the breastpump system 110 and/or the kit according to the user profile.

Generally, the breastpump system 110 may store certain baseline operation data that the breastpump system 110 may analyze during operation to detect fault conditions or errors. For example, baseline operation data associated with a pressure detected by a pressure sensor of the breastpump system 110 may be used to determine that a fault leak condition exists. In particular, the pressure from a pressure sensor may be below a baseline value by a threshold error coefficient for a threshold period of time. However, if profile data for example User A indicates that use of the breastpump system 110 by User A consistently results in lower than average pressure values, then the breastpump system 110 may adjust the leak condition values to account for the difference. In particular, the breastpump system 110 may modify its baseline values, error coefficients, or other data to account for the operating differences. Accordingly, the exemplary breastpump system 110 constructed in accordance with the principles herein may avoid erroneously triggering a fault condition resulting from lower pressure values when a fault leak condition does not actually occur. It should be appreciated that the user profiles may include additional parameters associated with operation of the breastpump system 210 including, for example, expressed milk volume, average pump time, average suction level, and/or others.

The user profile data may also be beneficial in a clinical setting such as a hospital, clinic, or other type of health care institution. Generally, a patient may have an associated electronic medical record (EMR) and/or electronic health record (EHR), where each of the EMR and the EHR may include a patient medical history that may be referenced and used for diagnosis and treatment. The EMR and/or the EHR of a patient may be included with the user profile of the patient or may be separate from the user profile of the patient. Accordingly, a kit identification of a particular user may additionally identify a corresponding EMR and/or EHR for the user.

When the breastpump system 110 detects the kit identification, the breastpump system 110 may identify the patient associated with the kit identification and connect to a server associated with the health care institution to retrieve data associated with the patient. In one embodiment, the breastpump system 110 may retrieve a set of configuration settings for the breastpump system 110 that are preferred by the patient or a clinician, and may configure itself accordingly.

In another embodiment, the breastpump system 110 may retrieve at least a portion of the EMR and/or EHR corresponding to the patient. It should be appreciated that the breastpump system 110 may be configured to comply with HIPAA and/or any other applicable healthcare-related laws or regulations that govern which patient data may be made available. The breastpump system 110 may further be configured to update any relevant data (e.g., the set of configuration settings and/or any relevant portions of the EMR and/or EHR, or kit ID) during and/or after a breastpumping session, and may communicate the updated data to the server associated with the health care institution. Accordingly, when the breastpump system 110 reconnects to the server (e.g., before a subsequent breastpumping session), the breastpump system 110 may retrieve relevant updated data.

In certain situations where there may be multiple breastpumps in the same location (e.g., in a hospital or a lactation room), the user 106 may have or wish to use a specific breastpump, such as a breastpump that is already configured according to the preferences of the user 106. Because the electronic device 105 may wirelessly connect to a breastpump, each of the breastpumps in the location may emit a connection signal, which may be a unique signal or a signal transmitted over a unique channel or frequency, detectable by the electronic device 105, where the electronic device 105 may measure the signal strength of each connection signal (e.g., in mV/m) to determine the preferred breastpump of the user 106. For example, the preferred breastpump may be the breastpump that is closest to the user 106 and thus the breastpump that emits the connection signal having the highest received signal strength.

In certain situations, the breastpump system 110 may experience a fault, error, breakdown, or the like, which may prompt its user to contact customer service or support. These situations may be tedious and time consuming to the user because the user may need to troubleshoot the breastpump system 110 and/or may want or need to order/request a new or replacement breastpump, even if there is no mechanical defect in the breastpump system 110. Similarly, a manufacturer, retailer, or servicer of the breastpump system 110 may need to dedicate resources for providing support to the users. As a result, a goal of a manufacturer, retailer, or servicer of the breastpump system 110 may be to reduce the number of situations in which a user of the breastpump system 110 may need service or support for the breastpump system 110. The present embodiments therefore provide various techniques to preemptively identify circumstances or situations which may cause a user of the breastpump system 110 to contact customer support or service. In addition, the present embodiments provide a means of distinguishing between conditions that are in fact faults and those that do not require additional support or service but merely user intervention, such as certain leaks that may arise during a pumping session.

According to embodiments, certain components of the breastpump system 110 may be configured with a set of sensors. For example, the set of sensors may include one or more pressure sensors disposed at any location within or along the tubing 113, 114 of the breastpump system 110 (or another portion of the breastpump system 110), where the pressure sensors are designed to detect the amount of pressure within the tubing 113, 114. The pressure sensors can be positioned anywhere within an air fluid path that is directly or indirectly connected to the tubing. It should be appreciated that additional sensors are envisioned, such as overflow sensors, bacteria sensors, vibration and audio sensors, and/or others. Additionally, the breastpump system 110 may include a controller or processor configured to analyze data from the set of sensors and make various determinations based on the sensor data.

The controller of the breastpump system 110 may compare data collected from the set of sensors to baseline data in an attempt to identify potential or impending problems or issues with the breastpump system 110. In embodiments, the controller may be a proportional-integral-derivative (PID) controller which may employ a control loop feedback mechanism to calculate an error value or coefficient representing the difference between a measured process variable and a desired set point. It should be appreciated that other types of controllers are envisioned.

The controller may compare the error coefficient to a threshold value. In certain embodiments, the controller may account for a time metric in performing the error coefficient analysis in order to gauge any decline in performance over time and/or the current performance for a corresponding time period. If the error coefficient meets or exceeds the threshold value for a certain amount of time, or if the data indicates a gradual decline in performance, then the controller may deem that the breastpump system 110 (or a portion thereof) is faulty, may need immediate repair or replacement, or may need repair or replacement at a future time. Accordingly, the controller may facilitate various preemptive actions that may negate the need for the user to contact service or support.

In some embodiments, the controller may identify, based on the type of sensor data and the error coefficient analysis, that a certain part or component of the breastpump system 110 is faulty and therefore may need to be replaced. In response, the controller may request an entity (e.g., a manufacturer, retailer, or servicer of the breastpump system 110) to contact the user to arrange for a replacement part or component. For example, a service individual may call the user to inform the user of the potential issue and arrange for shipment of the replacement part or component. For further example, the controller may automatically generate an electronic communication (e.g., e-mail, text message, push notification) and send the electronic communication to the user (e.g., to the electronic device 105) to inform the user of the potential issue and arrange for shipment of the replacement part or component. It should be appreciated that the controller may determine that one or more parts of the breastpump system 110 may need replacement, or may determine that the entire breastpump system 110 may need replacement. This determination may be made, for example, based on the sensor or operation data collected from the various sensors as well as the error coefficient analyses.

As a result of the manufacturer, retailer, or servicer contacting the user before the user is compelled to contact service or support (or, in some cases, before there is a detectable problem with the breastpump system 110), the amount of time and effort that the user would otherwise spend on troubleshooting or replacing the breastpump system 110 may be reduced or eliminated. Additionally, the amount of support resources needed by the manufacturer or retailer may be reduced, which may result in a cost savings passed down to the users or customers.

In one implementation, a dedicated breastpumping application of the electronic device 105 may interface with additional applications installed on the electronic device 105 (e.g., via an operating system of the electronic device 105). The user 106 may configure the electronic device 105 to cause the breastpump system 110 to stop or pause operation if certain conditions are detected. For example, if the electronic device 105 receives an incoming communication (e.g., phone call, text message, e-mail), then the electronic device 105 may automatically cause the breastpump system 110 to pause operation, or to place the breastpump 100 into a "quiet" mode in which audio cues of the breastpump system 110 may be muted. In some embodiments, the electronic device 105 may prompt the user 106 to select whether to pause operation of the breastpump system 110 in response to various detected conditions.

The electronic device 105 may also analyze data collected or sensed by various sensors to control certain operations and functionalities. In particular, the electronic device 105 may be equipped with various sensors including an imaging sensor(s), a barometer, an altimeter, a location module (e.g., a GPS chip), an accelerometer, a gyroscope, an audio module, including a microphone and speaker(s), and/or other sensors. The electronic device 105 may analyze any collected sensor data to determine an environment of the electronic device 105 and cause the breastpump system 110 to modify its operation accordingly, such as automatically increasing the volume of the breastpump system 110 audio during operation when the environmental noise is so high that audio feedback signals, such as leak alerts, cannot be heard during operation.

In one embodiment, the electronic device 105 may identify its current location (e.g., via GPS coordinates) and may examine a map database to identify a venue or location where the electronic device 105 may be located, and correspondingly where the breastpump system 110 may be located. For example, a user may have a user profile that indicates a home address and a work address, where the electronic device 105 may determine from the location data whether the electronic device 105 is located at home or at work. The electronic device 105 may appropriately configure the breastpump system 110 according to a "home configuration" that the user prefers at home or to a "work configuration" that the user prefers at work. In particular, the electronic device 105 may transmit a corresponding set of configuration settings to the breastpump system 110 based on identified location.

The electronic device 105 may be configured to estimate an ambient pressure based on alternative or additional data. For example, the electronic device 105 may determine its traveling velocity and if the traveling velocity exceeds a certain threshold (e.g., 250 miles/hour), then the electronic device 105 may deem that it is in flight and that its ambient pressure is lower than normal operating air pressure for the breastpump system 110. Accordingly, the electronic device 105 may cause the breastpump system 110 to modify its operation accordingly, such as by increasing or decreasing certain baseline operation data, error coefficients, and/or other data.

The electronic device 105 may also be configured to interface with an additional electronic device to retrieve relevant data and control operation of the breastpump system 110 accordingly. In one embodiment, the electronic device 105 may interface with a "wearable" device with stored activity data for its wearer (e.g., the user 106). The activity data may include, for example, movement data (e.g., in the form of "steps"), blood pressure readings, heart rate readings, and/or the like. The activity data may also have an associated timestamp such that when the electronic device 105 retrieves the activity data, the electronic device 105 may determine a current or recent activity state of the user.

Depending on the current or recent activity state of the user, the electronic device 105 may cause the breastpump system 110 to modify various operation parameters accordingly. For example, if the electronic device 105 indicates that the user has been active recently (e.g., has just finished an exercise session), then the electronic device 105 may increase (or decrease) a timeout parameter of the breastpump system 110, may increase (or decrease) a suction level of the breastpump system 110, and/or may modify other operation parameters, error coefficients, and/or the like.

In another embodiment, the electronic device 105 or breastpump system 110 may record data associated with an external audio device to identify a condition of which the user 106 may want to be alerted. For example, a microphone of the electronic device 105 may detect audio that is output from a baby monitor or similar device, where the electronic device 105 may analyze the audio and determine that a baby may need to be attended to. In some implementations, the electronic device 105 may detect sound/audio directly from the baby. The electronic device 105 may accordingly cause the breastpump system 110 to automatically pause operation which may enable the user 106 to attend to the baby, or at least prompt the user with an audio and/or visual cue to check whether the user would like to pause operation.

In another implementation, the microphone of the electronic device 105 may detect audio associated with operation of the breastpump system 110 and/or components thereof, and analyze the audio to determine an operating condition of the breastpump system 110. Based on the determination, the electronic device 105 may then modify operation of the breastpump system 110 accordingly. For example, the electronic device 105 may analyze detected audio and determine that the audio includes patterns consistent with a leak in the tubing 113, 114 of the breastpump system 110. As a result, the electronic device 105 may cause the breastpump system 110 to pause or stop operation, to modify operation (e.g., increase pump level) to account for the leak, or to modify operation in some other manner.

The present embodiments further contemplate systems and methods for labeling and tracking the bottles of collected milk that result from one or more breastpumping sessions. According to one implementation, the electronic device 105 may be configured to connect to a printer device via any type of wired or wireless connection. For example, the printer device may be a standard printer, a "pocket" printer that offers more portability, a label printer, or any other type of device capable of printing graphics or text on paper or similar physical media.

In response to a user entering various data associated with a breastpumping session (e.g., time, date, volume, or location) into the breastpumping application of the electronic device 105, the electronic device 105 or breastpump system 110 may generate a unique identification (e.g., an alphanumeric code or graphic) that corresponds to mom, bottle, pump and the breastpumping session. Additionally, the electronic device 105 may upload the unique identification and the various data related thereto to the processing server 115 for storage in the database 112. The electronic device 105 may further transmit instructions and imaging data to the printer device to cause the printer device to print out a label that corresponds to the breastpumping session.

In some embodiments, the label may include or indicate the unique identification generated by the electronic device 105, and may further include or indicate some or all of the various data associated with the breastpumping session. In other embodiments, the label may enable a user to access the unique identification and/or the various data (e.g., such as if the label is embodied as a QR code or other type of bar code). The user 106, the printer device, or another component may then manually or automatically apply the label to a corresponding bottle (e.g., one of the bottles 103, 104) that contains the milk collected during the breastpumping session.

In operation, a user (e.g., the user 106, a clinician, a nurse) may access or review some or all of the various data associated with the breastpumping session via the label that was printed. In one exemplary embodiment, a nurse may scan a label on a bottle and access the corresponding unique identification using a scanner or other electronic device. The scanner may then retrieve, using the unique identification, the various data associated with the corresponding breastpumping session, such as by retrieving the various data stored on a server in a hospital. The nurse may then use the retrieved data to properly or accurately administer a feeding, such as by using the freshest milk, distinguishing the bottle from bottles belonging to other mothers, or making other determinations. In another example embodiment, the labels and associated breastpumping session information may enable moms to distinguish their bottles from those of other moms (e.g., such as in a workplace environment), or may enable caregivers to distinguish bottles intended for certain babies (e.g., such as in a daycare).

The following terms relate to breastmilk expression system diagnostics:

Control Volume: total working space enclosed by the breastmilk expression system.

Volume: space occupied by a fluid.

Liquid Volume: space occupied by an incompressible fluid.

Gas Volume: space occupied by a compressible fluid.

Leak: flow of fluid into or out of the system control volume unrelated to the desired physiological response.

Leaked Volume: space occupied by a fluid entering or exiting the control volume.

Occlusion: partial or total blockage of passages resulting in reduced fluid communication between system elements.

Expressed Volume: space occupied by a liquid entering or exiting the control volume as a result of a physiological response to the breastmilk expression system.

During operation of the breastpump system 110, there may be conditions which affect the performance of the breastpump system 110 and/or the amount of milk collected. These conditions include: the leak of fluid into or out of the system control volume, the occlusion of the portions of the system intended to be in fluid communication, attachment of system elements which result in an excessively small or large control volume. There are various categories or causes for leaks including: the breastshield 107, 108 not being secured to the breast(s); the user 106 is single breastpumping but the breastpump system 110 is not set for single pumping; a vacuum is almost achieved but there is a leak in the system, such as when the tubing 113, 114 is slightly displaced from the connection port; or the breastpump system 110 is broken. Occlusions of the system may occur when tubes are kinked or crushed, etc. Excessive or inadequate control volume can occur if, e.g. breast shields which are not intended for use with the breastmilk expression system are utilized and are of a different volume. Any of these categories or causes may result in a less than optimal breastpumping session and possibly even a service call because the user may think that there is a problem with the breastpump system 110.

Unlike known systems that merely continue to operate despite the presence of a leak, occlusion or incorrect control volume, the current embodiments support various components and calculations, where required, to accurately assess leak characteristics and enable associated responses. The current embodiments can be configured to distinguish between the type of leak detected by a leak detection circuit, and a specific response to address the leak detected using a response circuit. The response generated by the response circuit can include providing feedback regarding the magnitude and type of the leak to the system, the user, or both the system and the user. Further, the current embodiments can employ solutions enabled by the response circuit for promptly addressing a variety of leaks, either directly or indirectly, once detected.

During operation of the breastpump system 110, the path of fluid communication between the breastpump system 110, and the breast may be occluded, as in kinked tubing, 113,114. Unlike known systems that merely continue to operate despite the presence of an occlusion, the current embodiments support various components and calculations, where required, to accurately assess whether an occlusion is present. The current embodiments can be configured to distinguish an occlusion from leaks and to provide feedback regarding the magnitude and nature of the occlusion. Further, the current embodiments can employ solutions for promptly addressing a variety of occlusions, either directly or indirectly, once detected.

The current embodiments enable the user to effectively and efficiently intervene with feedback selectively provided via the response circuit throughout the pumping session so that the user may eliminate or mitigate leaks or occlusions without having to take the extra time to deduce whether there is something wrong with the breastpump system 110.

In various embodiments a leak may be detected prior to normal breast pumping operation. This may be achieved by closing the breastpump system from the atmosphere and conducting various operations. The closing of the breastpump system may be accomplished by, for instance, plugging the breastshields, closing a valve between the pump and the breastshield either manually or automatically, as by a solenoid valve, cinching the tubing leading to the breastshields. Once the system is isolated from the atmosphere, the pump can be caused to displace a known quantity of volume and then the vacuum measured. If there is no leak or an adequately small leak, a predictable vacuum will be achieved in the breastpump system. This level of vacuum will be dependent on the original atmospheric pressure in the system, the original volume, and the volume after displacement. Additionally, the pump could be made to achieve a particular vacuum and the displaced volume can be detected in order to achieve that vacuum. Leaks may be introduced after re-configuring the system for normal use. Further, leaks may develop between reconfiguring the pump and conducting normal breastpumping.

In another embodiment, the breastpump can control to a fixed vacuum during normal breastpumping, and determine the rate of displacement required to achieve the fixed vacuum. This rate of displacement will be proportional to the leakage rate.

In another implementation, the breastpump can assume a fixed displacement which has generated a vacuum in the pump and observe the rate of change of the vacuum. If the pressure is increasing over time, the leak rate will be associated with the rate of increase of pressure at a given moment. The leak rate will depend on the atmospheric pressure and the original volume of the pump system.

According to embodiments, the breastpump system 110 is configured to determine leaks while the breastpump system 110 is operating, including intermittent leaks where the breastpumping session may be able to continue to operate in an effective manner. In particular, the breastpump system 110 may estimate a volume or degree of the leak by calculating the rate at which air/fluid enters the system and how it relates to the vacuum and piston displacement. Using this information, the breastpump system 110 is able to estimate the attached volume and leak size by estimating the state of the system and making comparisons to measured state variables, and/or stored information based on the pumping configuration, e.g. an expected minimum pressure, a pressure vs. time profile, or an intended displacement. The state of unmeasured variables may be then updated to minimize the error in the estimate when compared to the measurements, resulting in an estimate of the magnitude of the leak and the attached volume. The breastpump system 110 is therefore able to identify a likely source of the leak as well as adjust operation of the breastpump system 110 accordingly so as to counteract the leak.

The embodiments described above can be combined in an advantageous manner. E.g., the breastpump could be controlled to a specific volume simultaneous with estimation of leak and pressure parameters, the breastpump could be controlled to a specific pressure combined with the estimation of leak and volume parameters.

The embodiments described herein differ from conventional leak detection techniques in that the embodiments herein are capable of distinguishing between different types of leaks, and/or sizes of leaks, and based on the detected nature and/or size of the leak, a controller can operate the breastpump to either perform a system change, provide feedback to the system, the mom using the system, or both, or perform a system change and provide feedback. In certain embodiments the system can continuously or substantially continuously deduce the difference between the required volume displacement to generate the desired vacuum curve and the volume displacement required to generate the desired vacuum curve in a non-leaking breastpumping system. The embodiments may estimate parameters for the original system volume and the leak magnitude based on the observed vacuum at a particular displaced volume.

The embodiments disclosed herein may therefore permit the user to customize the user's experience by continuously analyzing the system for leaks throughout, or during discrete or random intervals during the breastpumping session, and dynamically notifying the customer of a distinct detected leak with an appropriate message, sound, or internal corrective measure. This enables the breastpump system 110 to deduce when the user is having a physiological response that is not a leak, and enables the breastpump system 110 to delay a shut off in the event that the user is not yet connected by determining, via sampling or another suitable method, that the user has not yet connected to the breastpump system 110 after the breastpump system 110 is activated. An event such as a loss of seal between the breast shield and the breast could also be detected as a type of leak that would cause an immediate response, such as a cessation of operation and a return of the vacuum source to a home position.

In one implementation, the user of the breastpump system 110 can input the size of the breastshields 107, 108, or the breastpump system 110 may automatically identify this information from a connected device or accessory and store in its settings. To determine a vacuum or vacuum level while in operation, the breastpump system 110 may include a pressure measurement component (such as a component(s) 234 as shown in FIG. 2) configured to generate at least one reading during operation of the breastpump system 110. The pressure measurement component may include one or more of the following: a pressure switch, a two setting pressure switch, a relative pressure sensor, an absolute pressure sensor, and at least two pressure sensors. Additionally, to determine the vacuum or vacuum level while in operation, the breastpump system 110 has the ability to detect a load on the motor. In some implementations, the breastpump system 110 may determine the vacuum or vacuum level from detecting a force or strain in a volume displacement device, a change in temperature, or a motor armature current, or other.

In implementations in which the breastpump system 110 is a positive displacement pump, a controller of the breastpump system 110 may determine whether there is a leak by determining the displaced volume of the pump, estimating or determining the original volume of the pump kit system, determining the vacuum over time, and solving for the difference between the current volume and the volume that would produce the measured vacuum.

If the controller determines that there is a leak, the controller may cause the user interface 109 to indicate the leak, such as by activating a light, displaying an error (e.g., "ERR"), sounding a tone, or via other audio, visual cues, or other feedback. The controller may continue operation of the breastpump system 110 while the user mitigates or eliminates the leak, such as via incorporating a threshold timeout. Additionally, the controller may determine that the leak is milk entering the system, as discussed in detail below.

The controller may continuously determine if there is a leak by continuously determining the atmospheric pressure, displaced volume, initial volume (which may be estimated or determined from any suitable means such as the size of the breastshields, or determined from information stored with the breastshields or system configuration, or any other suitable means) and vacuum.

In one implementation, the controller may consistently and periodically perform this determination. For example, the controller may constantly perform this determination every four (4) ms. In another implementation, the controller may repeatedly perform this determination a set number of times after a set period of time has elapsed. In other words, there may be dwell times between determinations. For example, the controller may perform this determination a total of five (5) times every three (3) ms, then wait a total of fifteen (15) ms, then perform this determination an additional five (5) times every three (3) ms, then wait another fifteen (15) ms, and so on, in what may be considered a "train" of determinations. It should be appreciated that the amount of time between determinations and the amount of time during which the controller does not perform any determinations may vary and may also be configurable or be random.

The closer the intervals are between determinations, the greater the resulting pump monitoring and performance until the intervals reach a point where incremental differences are barely discernible in the resulting performance. If there is a leak the controller may determine both the size of the leak as well as an operation to perform based on the size of the leak. In some scenarios, the size of the leak may be below a threshold value and the controller may therefore not take any action.

In other scenarios, the leak may meet or exceed a threshold value and the controller may take various actions including pausing or stopping the pump, increasing or decreasing a suction level, indicating the leak via the user interface 109, maintaining operation or idling while enabling the user to mitigate or eliminate the leak, applying more or less torque, increasing or decreasing a current level, causing the user interface 109 to indicate the leak, or performing other actions. The controller may also collect and analyze subsequent data or readings to determine whether the leak has been corrected or otherwise adequately mitigated. In some implementations, the controller may account for operation data within a user profile of the user of the breastpump system 110 when determining whether there is a leak. In particular, operation of the breastpump system 110 by certain users may result in certain piston positions, or displacements of the vacuum generating member, and vacuums that, in "normal" usage, may correspond to a leak in the breastpump system 110. However, for the certain users, these piston position and vacuum may result in non-leak operation of the breastpump system 110. Therefore, the controller may make adjustments to any baseline values, error coefficients, or other variables during the leak determination so that the controller does not erroneously trigger the detection of a leak.

A new and useful feature to include in a breastmilk expression system would be the ability to measure at least one of milk volume, flow rate, and milk ejections in a non-contact manner. Such a solution would minimize the chance of milk contamination, reduce cleaning burdens, and help to simplify the overall user experience of a breastmilk expression system while avoiding added costs of additional sensors in the system.

In an embodiment, a closed loop breastmilk expression system can be utilized to indirectly measure breastmilk output during a pumping session. Given that the pump, pump kit, and lactating breast effectively define a closed system, i.e. a control volume, the pressure-to-volume relationship can be established for a positive displacement system.

The closed system is a mixed-phase system, wherein a vacuum (partial pressure) is periodically generated via air rarefaction within the control volume that also contains breast milk in a liquid state.

Breastmilk entering the system is effectively an incompressible substance and remains in a liquid state at the working pressures. Expected changes in the working pressure range, both positive & negative, have no appreciable influence on the volume of breastmilk. Therefore, volume occupied by the breastmilk within the system decreases the volume of gas occupying a given control volume. For a given displacement of the pump, the expected vacuum level can be compared to the actual vacuum level achieved. The measured change in volume can approximate the volume of breastmilk collected as an indirect measurement.

The control volume in a breast pump system is not ideal for indirect milk measurement since it is neither rigid nor stable. This is due to elastic breast tissue and other flexure in the system. The breast tissue may also change in compliance over the course of a pumping session. Other limitations include pressure drops in the system due to flow restrictions and the possible inclusion of flexible membranes or filters (media separation) to prevent milk overflow into the pump. Leaks in the system are also undesirable. These and other factors introduce noise in the system that should be managed to obtain an accurate milk output reading. In addition, small amounts of breastmilk are typically expressed each vacuum cycle. This makes the signal (which is intended to be indicative of milk volume) difficult to discern from the system noise for an indirect measurement approach. While indirect measurement accuracy is limited compared to direct measurement techniques, the practical application does not require high accuracy. The benefits of a non-contact, unobtrusive measurement system outweigh the system measurement limitations. A closed loop breastmilk expression system of the present disclosure can ascertain milk volume and flow signal information from other undesirable factors such as leaks and other noise in the system. The system and methods disclosed herein are presented to improve accuracy.

Most breastpump systems evacuate a breastpump kit that expresses a small amount of milk in one cycle from the breast. At the end of the cycle the breastmilk is ejected though a one-way valve (a check valve) into a collection container. The collection container is not usually part of the evacuated control volume, in order to minimize the power required for the system and to provide a consistent control volume for consistent application of vacuum since collection container sizes and manufacturers often vary.

Some systems do evacuate the collection container as well. These systems have a disadvantage in the amount of power required to apply vacuum (due to larger control volume) but the check valve for the vacuum cycle is not restricted to be between the kit and the collection container.

The following embodiments may be employed to obtain a milk volume measurement. The second and third approaches described below are structured to improve the signal/noise ratio compared to the first approach described below.

Figure 5:
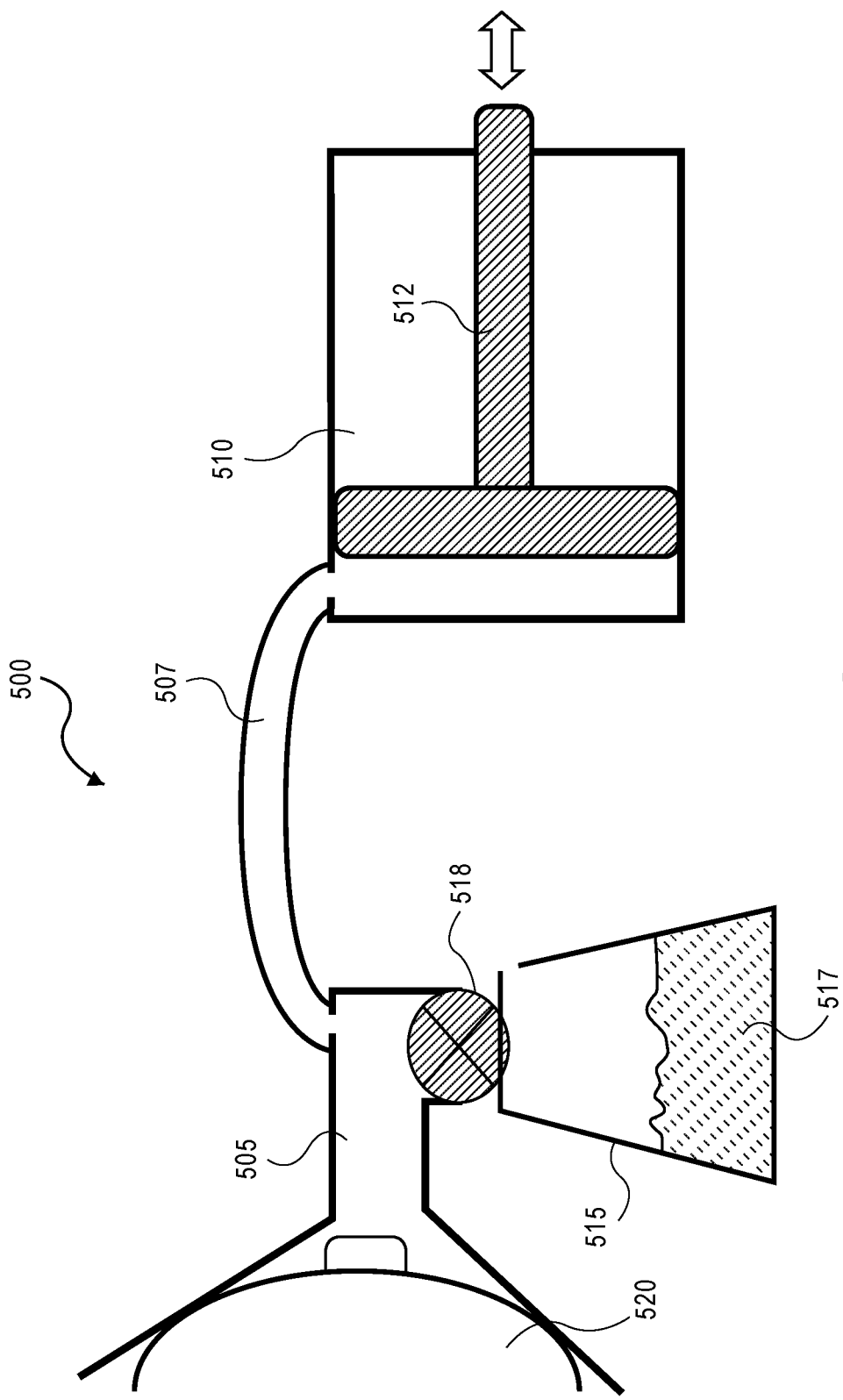
FIG. 5 is a semi-schematic view of a breastmilk expression system of the present disclosure operated in a first manner to measure the volume and/or flow rate and/or MER (milk ejection reflex) of expressed breastmilk.

A first method of measuring breastmilk volume involves taking a baseline vacuum-displacement cycle(s) reading(s) during the pumping session. This baseline reading would later be used to compare against other cycles to obtain the indirect milk volume measurement. Target cycles would include vacuum displacement where breastmilk is not introduced into the system, such that a baseline control can provide a more accurate comparison. The system may determine this or the input may in part come from the user—for example as they switch from stimulation to milk expression modes. Volume measurements would be captured over time throughout the pumping session. A typical system configured to use this approach is illustrated in FIG. 5.

Figure 6:
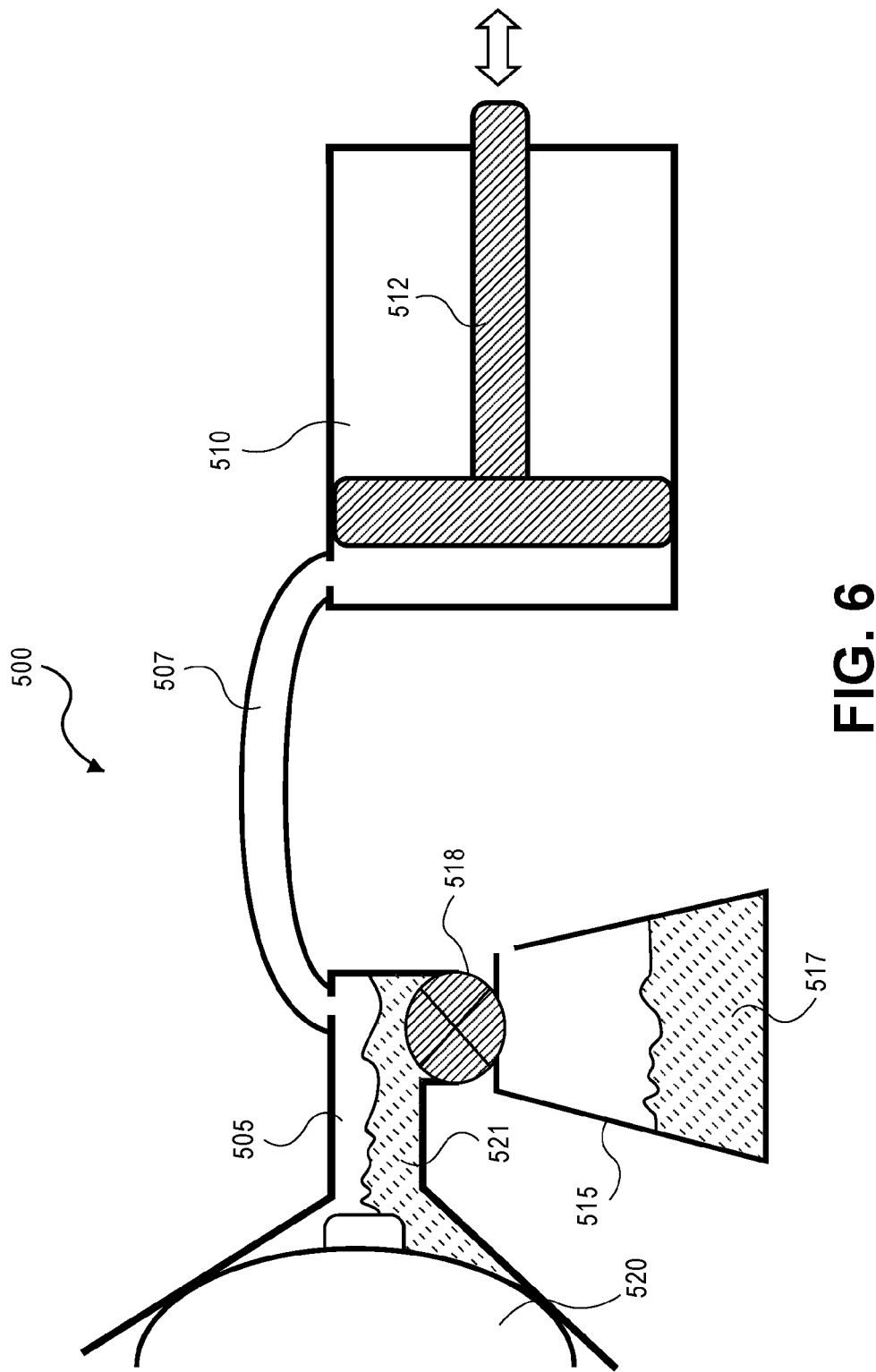
FIG. 6 is a semi-schematic view of a breastmilk expression system of the present disclosure operated in a second manner to measure the volume and/or flow rate and/or MER (milk ejection reflex) of expressed breastmilk.

A second approach is illustrated in FIG. 6. Since small volumes of breastmilk are typically expressed in each cycle, an improved approach would be to begin to pool (accumulate) the breastmilk in the kit for a plurality of cycles prior to ejecting the breastmilk into the collection container. One manner of accomplishing this, in a passively valved system, is to use a baseline vacuum to keep the check valve closed. This baseline vacuum need only be sufficient to overcome the head height pressure of the pooled breastmilk and valve closing forces. Once sufficient breastmilk has pooled, or after a determined number of cycles, the vacuum would return to equilibrium to allow the breastmilk to release into the collection container. In this way the determined change, or delta, of the control volume at the beginning of the accumulation compared to the end can provide a larger value, thereby increasing signal to noise of the system measurement.

In an embodiment an actively valved system would simply remain closed until it was determined to open the valve. Opening of the valve could occur either manually or automatically (i.e. such as by user intervention, electromechanically, or mechanically). In this exemplary embodiment the system would not necessarily require a baseline vacuum to keep the valve closed & could return to equilibrium each cycle.

By accumulating milk at the breast shield, several secondary benefits can be realized: The pump is more efficient as the milk accumulates due to a reduced effective control volume; accumulating milk could be contained in such a way as to warm the nipple; accumulating milk could be contained in such a way as to lubricate the nipple.

Figure 7:
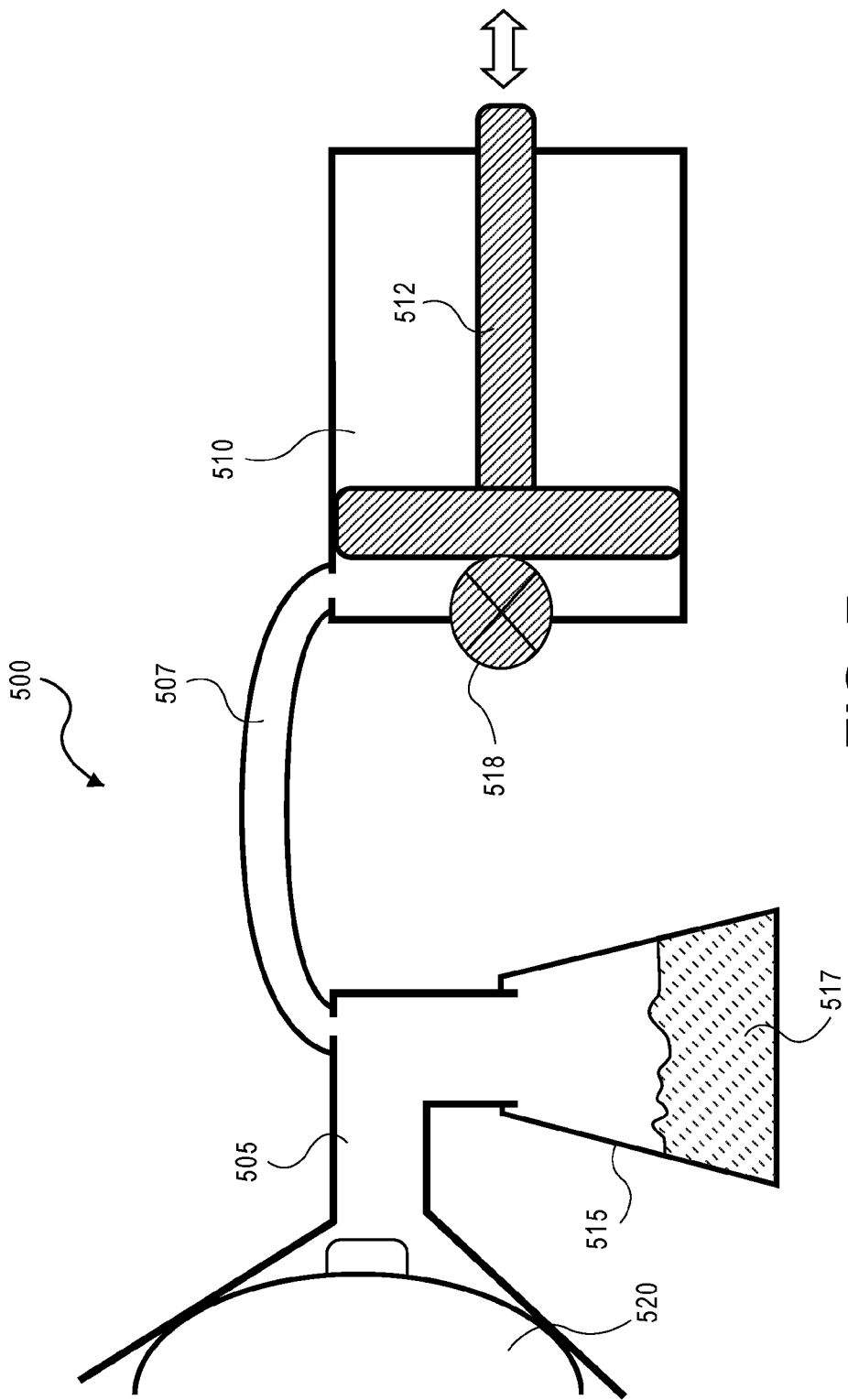
FIG. 7 is a semi-schematic view of a breastmilk expression system of the present disclosure operated in a third manner to measure the volume and/or flow rate and/or MER (milk ejection reflex) of expressed breastmilk.

According to a third approach, as illustrated in FIG. 7, the breastpump system could also accumulate milk in the collection container and compare the delta of an empty collection container at the beginning of a pumping session to that at the end. This approach is similar to the second approach, in that it would further increase measurement signal to noise. In a system operating according to this third approach, the check valve would not be intermediate to the kit and the collection container, but would instead be located elsewhere in the control volume. This approach requires evacuation of the collection container. While this system requires more power comparatively, it would become more efficient over time as the collection container fills with milk and reduce the effective control volume.

Other real time milk flow performance data could inform the system or reinforce/combine with the measurement techniques to provide even greater accuracy or augment the information. See U.S. patent application Ser. No. 14/208, 054, entitled "System and Method for Managing a Supply of Breastmilk", which is incorporated in its entirety herein by reference. In one embodiment, an imaging system could help tune the user-breast pump system to provide higher accuracy in the milk estimation algorithms. For example, real time breastmilk flow could feed back to the system estimated milk flow to provide unique user-system correction factors. It can also be envisioned that despite some of the drawbacks of using direct measurement techniques such as flow meters or fluid level indicators, it would be advantageous to use them for limited duration for the same purpose of data correlation and tuning.

In combination with the above methods, other sources of information can improve accuracy. In session or multi-session feedback could be used to improve milk volume and flow estimates for a user. Actual results can be compared to estimated results and correction factors employed. Also, corrections for temperature effects and leaks may be employed. Finally, specific vacuum or pressure profiles may be employed to test and quantify specific factors such as control volume estimates, system leaks, or to isolate variables. For example, the system may be used in a state where positive or negative pressure is applied in such a way that milk would not be expressed from the breast and the control volume response could be more accurately identified. It is important to distinguish between leaks and milk entering the system in order to improve volume and flow measurement accuracy. In addition to the system providing estimates of milk volumes, flow rates, and milk ejections; the accuracy of those measurements may also be reported out. Any suitable communication or storage transfer method can be employed to report out the measurements.

In addition to using any of the above-described exemplary approaches to calculate milk volume for an entire pumping session, they could be used to calculate milk volume for a portion of a pumping session, and could be combined with additional data, such as elapsed time of a pumping session, to determine expression rate, number of milk ejections, duration of milk ejections, and other data points that may be meaningful metrics in evaluating the quality, effectiveness, and/or efficiency of a pumping session.

Figure 8:
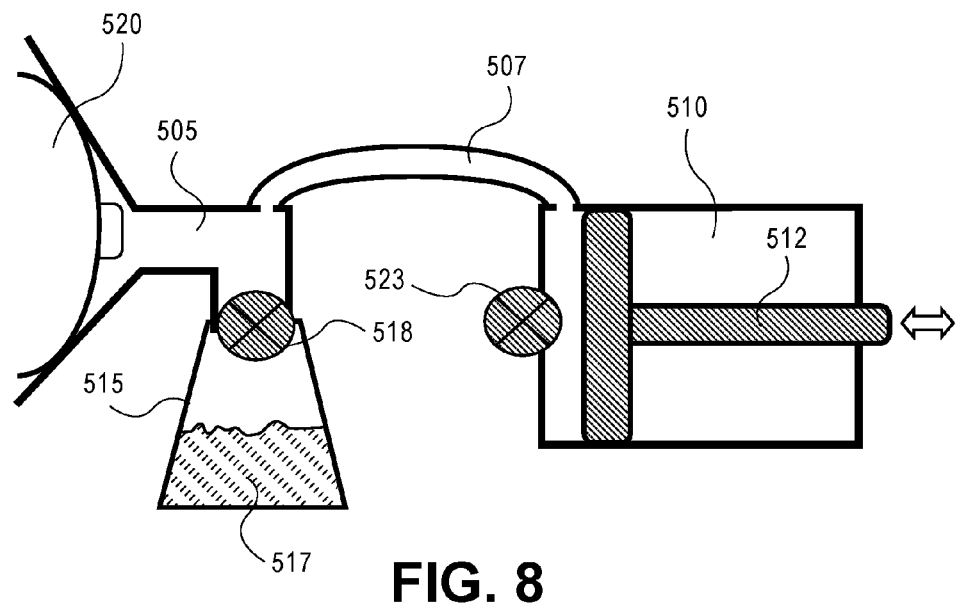
FIG. 8 is a semi-schematic view of a breastmilk expression system of the present disclosure operated in a fourth manner to measure the volume and/or flow rate and/or MER (milk ejection reflex) of expressed breastmilk.
Figure 9:
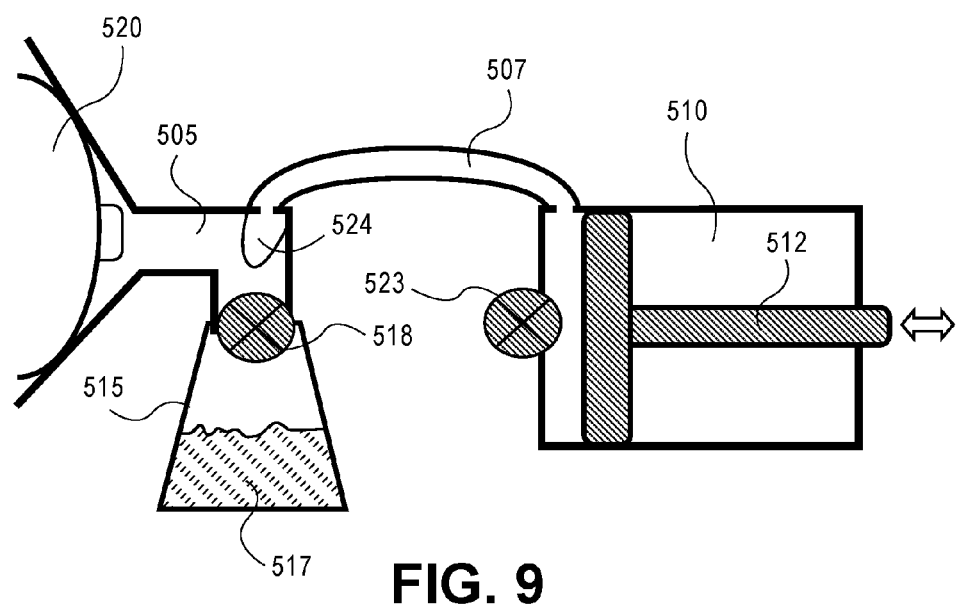
FIG. 9 is a semi-schematic view of a breastmilk expression system of the present disclosure operated in a fifth manner to measure the volume and/or flow rate and/or MER (milk ejection reflex) of expressed breastmilk.

Other system configurations such as those shown in FIGS. 8 & 9 are also envisioned, and may be used in the embodiments previously described. These system semi-schematics are not exhaustive and further combinations exist.

Therefore, the exemplary embodiments enable the detection and computational analysis of milk volume and/or milk flow, modest, manageable leaks, and larger, unacceptable leaks. The embodiments further enable a variety of custom settings where tolerance may be allowed for certain leaks for a specified period of time, if desired, or alerts can be generated, as desired, based on milk volume and/or milk flow. This enables the breastpump system 110 to avoid certain shut off conditions where the user may not yet be connected, and to incorporate other flexible customized leak, milk volume and milk flow feedback and control. As a result, the breastpump system 110 is more adaptive to the user and allows for expectations of intended pump operation to be incorporated into the pumping session parameters.

In some implementations, the breastpump system 110 (as well as additional breastpumps) may provide any collected or determined information to the processing server 115, and the processing server 115 may analyze any received information to determine leak cause frequency, milk output, or other metrics that provide feedback that may lead to potential design enhancements or adjustments to the breastpump system 110 or any components thereof.

Figure 4:
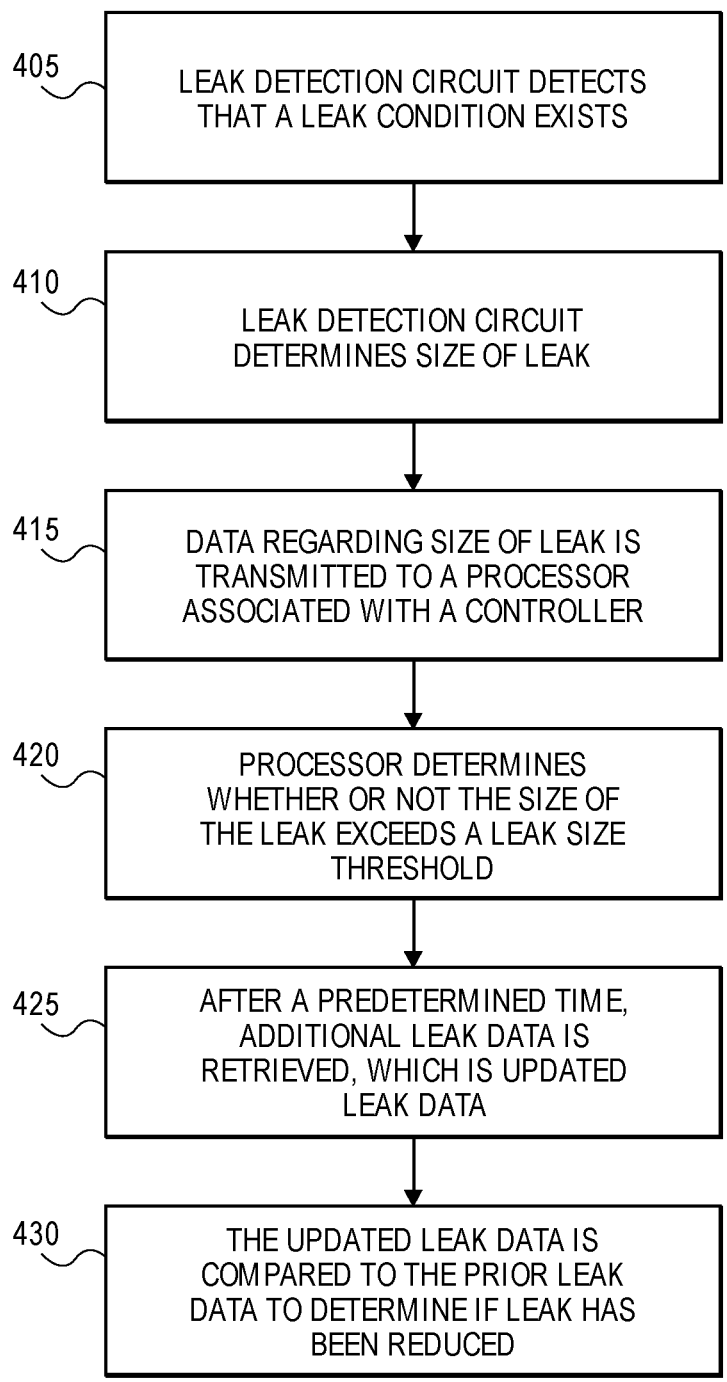
FIG. 4 is a flow diagram of an exemplary method to distinguish a leak during operation of an improved feedback milk extracting system with a response circuit constructed in accordance with the principles of the present disclosure.

FIG. 4 depicts a method 400 of distinguishing a leak within a breastpump system. It should be appreciated that the method 400 may be performed by the breastpump system itself, and in particular various components of the breastpump system. It should be appreciated that the method 400 is merely exemplary and that additional or alternative functionalities are envisioned.

The method 400 may begin with a leak detection circuit detecting (block 405) that a leak exists. The leak detection circuit may determine (block 410) a size of the leak. The leak detection circuit may also transmit (block 415) data regarding the size of the leak to a processor associated with a controller of the breastpump system.

The processor may determine (block 420) whether the size of the leak exceeds a leak size threshold. In embodiments, a predetermined amount of time may elapse after the processor determines whether the size of the leak exceeds the leak size threshold. After the predetermined amount of time has elapsed, the leak detection circuit may retrieve (block 425) additional leak data (i.e., updated leak data). The processor may compare (block 430) the updated leak data to the prior leak data to determine if the leak has been reduced.

FIGS. 5-9 illustrate various cross-section views of a breastpump system and its interaction with a user. It should be appreciated that the breastpump system as depicted in FIGS. 5-9 is merely exemplary and that additional or alternative components are envisioned.

FIG. 5 depicts a breastpump system 500 that may include a kit 505 connected to a pump 510 via tubing 507. The kit 505 may be positioned in proximity or secured to a breast 520 of a user. The pump 510 may include a piston 512 or plunger that may apply or release a force within the tubing 507 and the kit 505. When the piston 512 applies a force within the tubing 507 and the kit 505, a corresponding force may be applied on the breast 520, and fluid (milk) may be expressed from the breast 520 and may enter the kit 505. The breastpump system 500 may further include a collection container 515 that may collect fluid 517 that is expressed from the breast 520. A valve 518 may be positioned between the kit 505 and the collection container 515, where the valve 518 may control the transfer of fluid from the kit 505 to the collection container 515.

FIG. 6 depicts the breastpump system 500 as described with respect to FIG. 5. FIG. 6 illustrates the kit 505 filled with fluid 521 that was extracted from the breast 520. The fluid 512 may be maintained in the kit 505 by the valve 518 that is in a closed position (i.e., there is not a clear pathway between the kit 505 and the collection container 515). FIG. 7 depicts the breastpump system 500 with the valve 518 in the "open" position (i.e., the position of the valve 518 enables a clear pathway between the kit 505 and the collection container 515). Accordingly, the fluid 521 in the kit 505 as depicted in FIG. 6 may transfer to the fluid 517 in the collection container 515.

FIG. 8 depicts an alternative implementation of the breastpump system 500. In particular, FIG. 8 depicts the breastpump system 500 with two valves 518, 523, where the valve 518 may be positioned in relation to the kit 505 and the valve 523 may be positioned in relation to the pump 510. FIG. 9 depicts another alternative implementation of the breastpump system 500. In particular, FIG. 9 depicts a media separation 524 that may be part of the tubing 507. According to embodiments, the media separation 524 may control the suction force within the kit 505.

In general, the breastpump system 110 may include one or more processors (or controller(s) such as a hardware controller 232 as shown in FIG. 2) as well as a memory (such as a memory 230 as shown in FIG. 2) and a comparison circuit (such as a comparison circuit 235 as shown in FIG. 2). The memory may store an operating system capable of facilitating the functionalities as discussed herein as well as a set of applications (i.e., machine readable instructions). For example, one of the set of applications may be a leak detection application having a leak detection circuit and a response circuit configured to analyze data to detect leaks and/or facilitate various functionalities for mitigating the leak. It should be appreciated that one or more other applications are envisioned.

The processor may interface with the memory to execute the operating system and the set of applications. According to some embodiments, the memory may store pressure vs. time profiles, user profiles, various baseline data, and/or other data that the breastpump system 110 may utilize to support the systems and methods. Various of the applications may access the memory to facilitate the various applications discussed herein. The memory may include one or more forms of volatile and/or non-volatile, fixed and/or removable memory.

The breastpump system 110 may further include a communication module configured to communicate data via the one or more networks 120. According to some embodiments, the communication module may include one or more transceivers (e.g., WWAN, WLAN, and/or WPAN transceivers; such as a transceiver 231 as shown in FIG. 2) functioning in accordance with IEEE standards, 3GPP standards, or other standards, and configured to receive and transmit data via one or more external ports. For example, the communication module may receive, via the network 120, user profile data associated with a user of the breastpump system 110. The breastpump system 110 may further include the user interface 109 configured to present information to a user and/or receive inputs from the user. The user interface 109 may include a display screen and I/O components (e.g., ports, capacitive or resistive touch sensitive input panels, keys, buttons, lights, LEDs, speakers, microphones). In some embodiments, the breastpump system 110 may communicate with other hardware or software components within a "cloud" network.

In general, a computer program product in accordance with an embodiment may include a computer usable storage medium (e.g., standard random access memory (RAM), an optical disc, a universal serial bus (USB) drive, or the like) having computer-readable program code embodied therein, wherein the computer-readable program code may be adapted to be executed by a processor or controller (e.g., working in connection with an operating system) to facilitate the functions as described herein. In this regard, the program code may be implemented in any desired language, and/or may be implemented as machine code, assembly code, byte code, interpretable source code or the like (e.g., via C, C++, Java, Actionscript, Objective-C, Javascript, CSS, XML). In some embodiments, the computer program product may be part of a cloud network of resources.

Additionally, certain embodiments are described that may be implemented using logic or a number of routines, subroutines, applications, circuits or instructions. These may constitute either software (e.g., code embodied on a non-transitory, machine-readable medium) or hardware or both. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the terms "hardware module," "processor," and "controller" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

The embodiments herein have been described and shown for purposes of illustration only, and are not to be construed as constituting any limitations of the present principles. Modifications will be obvious to those skilled in the art, and all modifications that do not depart from the spirit of the principles herein are intended to be included within the scope of the appended claims. Those skilled in the art will appreciate that the conception, upon which this disclosure is based, may readily be utilized as a basis for the designing of other structures, methods and systems for carrying out the several purposes of the present principles.

Therefore, the foregoing is considered as illustrative only of the principles herein. Further, since numerous modifications and changes will readily occur to those skilled in the art, it is not desired to limit the principles to the exact construction and operation shown and described, and accordingly, all suitable modifications may be resorted to, falling within the scope of the principles described herein.

According to an embodiment, a breastmilk extracting system may be provided. The breastmilk extracting system may include a pressure measurement component configured to obtain a pressure level in the system during operation of the system; a comparison circuit configured to, on a substantially continuous basis, compare at least one of a displacement measurement and motor current data to the pressure level to obtain a comparison result, determine that there is a leak in the system when the comparison result at least meets a threshold value, and estimate a magnitude of the leak; and at least one feedback component configured to indicate to a user the existence of the leak in the system.

In an aspect, to estimate the magnitude of the leak, the comparison circuit may be configured to calculate a rate at which fluid enters the system, and compare the rate to a measured state variable.

In an aspect, the comparison circuit may be further configured to compare the pressure level to an expected pressure level, and based on the comparison, estimate a fluid flow volume in the system.

In an aspect, when the comparison result at least meets the threshold value, the comparison circuit may be further configured to determine, based on the comparison result, at least one action to take to address the leak in the system, and perform the at least one action.

In an aspect, to obtain the pressure level in the system during operation of the system, the pressure measurement component may be configured to obtain, at a first point in time, a first pressure level, and obtain, at a second point in time, a second pressure level; and wherein to compare the at least one of the displacement measurement and the motor current data to the pressure level, the comparison circuit may be configured to compare the at least one of the displacement measurement and the motor current data to the first pressure level and the second pressure level to obtain the comparison result.

In an aspect, the system may further include a milk flow loop configured to calculate a milk flow volume estimate by comparing the pressure level to an expected pressure level; and an output module configured to generate milk output data indicating at least one of milk flow, milk volume, and milk ejection reflex (MER), based on the milk flow volume estimate.

In an aspect, the system may further include a transceiver configured to receive, from an electronic device, a set of user configuration settings; and a hardware controller interfaced with at least the transceiver, and configured to, determine, from the set of user configuration settings, a set of operation settings for the system, and configure the system according to the set of operation settings.

In an aspect, the transceiver may be further configured to receive, from the electronic device, sensor data associated with a set of sensors of the electronic device; and wherein the hardware controller may further determine the set of operation settings for the system from the sensor data.

In an aspect, the pressure measurement component may be an absolute pressure sensor.

In an aspect, the pressure measurement component may be at least two pressure sensors.

According to another embodiment, a method for operating a breastmilk extracting system may be provided. The method may include obtaining, by a pressure measurement component, a pressure level in the system during operation of the system; on a continuous basis, comparing at least one of a displacement measurement and motor current data to the pressure level to obtain a comparison result; when the comparison result at least meets a threshold value, determining that there is a leak in the system, and estimating a magnitude of the leak; and indicating, to a user by at least one feedback component, the existence of the leak in the system.

In an aspect, estimating the magnitude of the leak may include calculating a rate at which fluid enters the system, and comparing the rate to a measured state variable.

In an aspect, the method may further include comparing the pressure level to an expected pressure level; and based on the comparing, estimating a fluid flow volume in the system.

In an aspect, the method may further include, when the comparison result at least meets the threshold value: determining, based on the comparison result, at least one action to take to address the leak in the system, and performing the at least one action.

In an aspect, obtaining the pressure level in the system during operation of the system may include obtaining, at a first point in time, a first pressure level; and obtaining, at a second point in time, a second pressure level; and wherein comparing the at least one of the displacement measurement and the motor current data to the pressure level may include: comparing the at least one of the displacement measurement and the motor current data to the first pressure level and the second pressure level to obtain the comparison result.

In an aspect, the method may further include calculating a milk flow volume estimate by comparing the pressure level to an expected pressure level; and generating milk output data indicating at least one of milk flow, milk volume, and milk ejection reflex (MER), based on the milk flow volume estimate.

In an aspect, the method may further include receiving, from an electronic device via a transceiver, a set of user configuration settings; determining, from the set of user configuration settings, a set of operation settings for the system; and configuring the system according to the set of operation settings.

In an aspect, obtaining the pressure level in the system during operation of the system may include obtaining, by one of an absolute pressure sensor or at least two pressure sensors, the pressure level in the system during operation of the system.

According to another embodiment, a method of detecting leaks within a breastmilk extracting system may be provided. The method may include determining, by a processor at a first point in time, (i) a first absolute pressure within the system and (ii) an initial displaced volume; determining, by the processor at a second point in time, (i) a second absolute pressure within the extracting system and (ii) a second displaced volume; determining an original volume of the system; estimating a leaked volume of the system; comparing a difference between the original volume and the leaked volume to a threshold value to determine if there is a leak in the system and to produce a resulting comparison where the leak is present; based on the comparing, determining an action to take to address the leak, where the action differs for leaks of different sizes; and performing the action.

In an aspect, determining the initial displaced volume may include determining, at the first point in time, a first position of a volume displacement mechanism within the system; and wherein determining the second displaced volume may include determining, at the second point in time, a second position of the volume displacement mechanism within the system.

In an aspect, determining the first absolute pressure may include detecting a measure of at least one of: a force in a volume displacement component of the system, a temperature drop, and a motor armature current; and calculating the initial displaced volume based on the measure.

In an aspect, comparing the difference between the original volume and the leaked volume to the threshold value may include determining that the difference exceeds the threshold value; and determining the action to take to address the leak may include determining to pause operation of the system.

In an aspect, performing the action may include pausing operation of the system; and displaying, in a user interface, a visual alert indicating the leak in the system.

In an aspect, comparing the difference between the original volume and the leaked volume to the threshold value may include determining that the difference does not exceed the threshold value; and determining the action to take to address the leak may include determining to increase a current applied to the system.

In an aspect, performing the action may include prompting, via a user interface of the system, a selection to continue operation of the system; and responding to the selection received from the user interface.

In an aspect, performing the action may include displaying, via a user interface of the system, an indication of the leak in the system; waiting a threshold amount of time; and ceasing operation of the system if a selection is not detected within the threshold amount of time.

In an aspect, the method may further include importing a user profile including system operating data associated with the user profile; and adjusting the threshold value based on the user profile.

In an aspect, comparing the difference between the original volume and the leaked volume to the threshold value may include comparing the difference between the original volume and the leaked volume to the adjusted threshold value to determine that there is the leak in the system.

In another embodiment, a breastmilk extracting system may be provided. The system may include a leak detection system connectable to a controller, the leak detection system configured to determine a leak arising during a cycle in the system during delivery of the cycle of a pumping pattern using a leak volume calculation.

In an aspect, the pumping pattern may be further defined by a pumping test pattern having an interval of no increase or decrease of vacuum level from which the leak can be determined.

In an aspect, the pumping test pattern may run for one cycle.

In an aspect, the system may further comprise a response circuit for determining a response path based on a magnitude of the leak.

In an aspect, the response circuit may be configured to selectively include data input received that is relevant to the leak in the system.

In an aspect, the response circuit may be configured to enable feedback regarding the magnitude of the leak.

In another embodiment, a breastmilk extracting system may be provided. The system may include a leak detection circuit configured to determine a leak; and a response circuit connectable to the leak detection circuit, the response circuit selectively providing feedback from the leak detection circuit during a pumping session while selectively enabling continued use of the system and corrective operation based on a magnitude of the leak detected by the leak detection circuit.

In an aspect, the response circuit may be configured to disable continued use of the system if the magnitude of the leak is above a threshold level, and if the leak is not reduced below the threshold level during a holding period.

In an aspect, the response circuit is configured to deliver the feedback as a feedback signal indicating the magnitude of the leak if the magnitude of the leak is below the threshold level.

In an aspect, at least one of the feedback signal and a device configuration signal may be transmitted from the system to at least one of an electronic device and a server associated with the system.

In an aspect, the feedback signal may include an audio signal.

In an aspect, the feedback signal may include an error message and color coded backlighting.

What is claimed is:

1. A breastmilk extracting system for extracting milk from a breast of a user, comprising:
   a pressure measurement component configured to:
      generate at least one reading in the system during operation of the system, and
      determine, from the at least one reading in the system, a vacuum level in the system during operation of the system,
      wherein the pressure measurement component comprises at least one of: a pressure switch, a two setting pressure switch, a relative pressure sensor, an absolute pressure sensor, and at least two pressure sensors;
   a memory;
   a comparison circuit interfaced with the pressure measurement component and the memory, and configured to,
      on a substantially continuous basis,
         compare the vacuum level in the system during the operation of the system to an expected vacuum level in the system to obtain a comparison result,
         determine that there is a leak in the system when the comparison result at least meets a threshold value, the leak representative of a flow of milk or air into or out of the system, and
         estimate a magnitude of the leak; and
   at least one feedback component configured to selectively indicate to the user the existence of the leak in the system.

2. The breastmilk extracting system of claim 1, wherein the pressure measurement component is further configured to obtain a pressure level in the system during operation of the system;
   and wherein the comparison circuit is further configured to:
      compare the pressure level to an expected pressure level, and
      based on the comparison, estimate a flow volume of milk in the system.

3. The breastmilk extracting system of claim 1, wherein when the comparison result at least meets the threshold value, the comparison circuit is further configured to:
   determine, based on the comparison result, at least one action to take to address the leak in the system, and
   perform the at least one action.

4. The breastmilk extracting system of claim 1, wherein the pressure measurement component is further configured to:
   obtain, at a first point in time during operation of the system, a first pressure level,
   obtain, at a second point in time during operation of the system, a second pressure level, and
   determine the vacuum level in the system from the first pressure level and the second pressure level.

5. The breastmilk extracting system of claim 1, wherein the pressure measurement component is further configured to obtain a pressure level in the system during operation of the system;

wherein the comparison circuit is further configured to:
calculate a milk flow volume estimate by comparing the pressure level to an expected pressure level;
and wherein the system further comprises:
an output module configured to generate milk output data indicating at least one of milk flow, milk volume, and milk ejection reflex (MER), based on the milk flow volume estimate.

6. The breastmilk extracting system of claim 1, further comprising:
a transceiver configured to receive, from an electronic device, a set of user configuration settings; and
a hardware controller interfaced with at least the transceiver, and configured to,
determine, from the set of user configuration settings, a set of operation settings for the system, and
configure the system according to the set of operation settings.

7. The breastmilk extracting system of claim 6, wherein the transceiver is further configured to receive, from the electronic device, sensor data associated with a set of sensors of the electronic device;
and wherein the hardware controller further determines the set of operation settings for the system from the sensor data.

* * * * *